United States Patent
Abazeed et al.

(10) Patent No.: US 9,439,909 B2
(45) Date of Patent: Sep. 13, 2016

(54) COMPOSITIONS AND METHODS FOR SENSITIZING A NEOPLASTIC CELL TO RADIATION

(71) Applicants: The Broad Institute, Inc., Cambridge, MA (US); The Brigham and Women's Hospital, Inc., Boston, MA (US)

(72) Inventors: Mohamed Abazeed, Cleveland, OH (US); Matthew Meyerson, Concord, MA (US); Drew Adams, Cambridge, MA (US)

(73) Assignees: The Broad Institute, Inc., Cambridge, MA (US); Dana-Farber Cancer Institute, Inc., Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/466,668

(22) Filed: Aug. 22, 2014

(65) Prior Publication Data

US 2015/0057486 A1   Feb. 26, 2015

Related U.S. Application Data

(60) Provisional application No. 61/868,906, filed on Aug. 22, 2013.

(51) Int. Cl.
| | |
|---|---|
| *A61N 5/00* | (2006.01) |
| *C07H 21/04* | (2006.01) |
| *C12Q 1/68* | (2006.01) |
| *A61K 31/5377* | (2006.01) |
| *A61N 5/10* | (2006.01) |
| *G01N 33/50* | (2006.01) |

(52) U.S. Cl.
CPC ............ *A61K 31/5377* (2013.01); *A61N 5/10* (2013.01); *C12Q 1/6886* (2013.01); *G01N 33/5011* (2013.01); *A61N 2005/1098* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2011/0136246 A1*  6/2011  Shibata ................ C12Q 1/6886
436/94

OTHER PUBLICATIONS

Abazeed et al (Radiation Oncology, Nov. 1, 2012, vol. 84, No. 3S, p. S179-S180, abstract 1034).*
Ihle et al (Molecular Cancer therapeutics, 2004, 3:763-772).*
Wang et al (Invest. Opthalmol. Vis. Sci., 2008, 94:1671-1678).*
Zhang et al (Oncology Reports, 2010, 24:1683-1689).*
Singh et al (Antioxidants & Redox Signaling, 2010, vol. 13, No. 11:1627-1637).*
Kang et al (Antioxidants & Redox Signaling, vol. 7, Nos. 11 & 12; 2005; p. 1664-1673).*
Gupta et al (Int. J. Radiation Oncology Biol. Phys, 2003, 56:846-853).*
Schuurbiers et al (Journal of Thoracic Oncology, 2009, 4:761-767).*
Carmichael, J. et al., "Radiation Sensitivity of Human Lung Cancer Cell Lines," Eur. J. Cancer Clin. Oncol., vol. 25, No. 3, pp. 527-534 (1989).
Duchesne, G.M. et al., "A panel of human lung carcinoma lines: Establishment, properties and common characteristics," Br. J. Cancer, vol. 56, pp. 287-293 (1987).
Gupta, A. et al., "The Ras Radiation Resistance Pathway," Cancer Research, vol. 61, pp. 4278-4782 (2001).
Hayakawa, K. et al., "The Prognostic Significance of Immunohistochemically Detected p53 Protein Expression in Non-Small Cell Lung Cancer Treated with Radiation Therapy," Anticancer Research, vol. 18, pp. 3685-3688 (1998).
Langendijk, H. et al., "Cell proliferation and apoptosis in stage III inoperable non-small cell lung carcinoma treated by radiotherapy," Radiotherapy and Oncology, vol. 56, pp. 197-207 (2000).
Matsuzoe, D. et al., "p53 mutations predict non-small cell lung carcinoma response to radiotherapy," Cancer Letters, vol. 135, pp. 189-194 (1999).
McDonald, J.T. et al., "Ionizing radiation activates the NrF2 antioxidant response," Cancer Res., vol. 70(21), pp. 8886-8895 (2010).
McKenna, W.G. et al., "The RAS signal transduction pathway and its role in radiation sensitivity," Oncogene, vol. 22, pp. 5866-5875 (2003).
Mitsuishi, Y. et al., "Nrf2 Redirects Glucose and Glutamine into Anabolic Pathways in Metabolic Reprogramming," Cancer Cell, vol. 22, pp. 66-79 (2012).
Singh, A. et al., "Gain of Nrf2 Function in Non-Small-Cell Lung Cancer Cells Confers Radioresistance, Antioxidants & Redox Signaling," vol. 13, No. 11, pp. 1627-1637 (2010).

* cited by examiner

*Primary Examiner* — Laura B Goddard

(74) *Attorney, Agent, or Firm* — Melissa Hunter-Ensor; Elbert Chiang; Greenberg Traurig, LLP

(57) ABSTRACT

The invention provides for the use of radiation sensitizing agents in combination with radiation for the treatment of neoplasia, methods for the identification of genotype-specific radiation sensitizing agents, and methods of identifying patients who could benefit from therapy with a genotype-specific radiation sensitizing agent.

18 Claims, 11 Drawing Sheets

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agagcaagat ttagatcatt t                                                  21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gctcctactg tgatgtgaaa t                                                  21

<210> SEQ ID NO 3
<211> LENGTH: 600
<212> TYPE: PRT
<213> ORGANISM: Homo sapiens

<400> SEQUENCE: 3

Met Met Asp Leu Glu Leu Pro Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Arg Lys Glu Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Leu Gln Leu Asp Glu Glu Thr
65                  70                  75                  80
```

```
Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
            100                 105                 110

Ala Leu Tyr Phe Asp Asp Cys Met Gln Leu Leu Ala Gln Thr Phe Pro
        115                 120                 125

Phe Val Asp Asp Asn Glu Val Ser Ser Ala Thr Phe Gln Ser Leu Val
    130                 135                 140

Pro Asp Ile Pro Gly His Ile Glu Ser Pro Val Phe Ile Ala Thr Asn
145                 150                 155                 160

Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
            180                 185                 190

Ser Ile Pro Glu Leu Gln Cys Leu Asn Ile Glu Asn Asp Lys Leu Val
        195                 200                 205

Glu Thr Thr Met Val Pro Ser Pro Glu Ala Lys Leu Thr Glu Val Asp
    210                 215                 220

Asn Tyr His Phe Tyr Ser Ser Ile Pro Ser Met Glu Lys Glu Val Gly
225                 230                 235                 240

Asn Cys Ser Pro His Phe Leu Asn Ala Phe Glu Asp Ser Phe Ser Ser
                245                 250                 255

Ile Leu Ser Thr Glu Asp Pro Asn Gln Leu Thr Val Asn Ser Leu Asn
            260                 265                 270

Ser Asp Ala Thr Val Asn Thr Asp Phe Gly Asp Glu Phe Tyr Ser Ala
        275                 280                 285

Phe Ile Ala Glu Pro Ser Ile Ser Asn Ser Met Pro Ser Pro Ala Thr
    290                 295                 300

Leu Ser His Ser Leu Ser Glu Leu Leu Asn Gly Pro Ile Asp Val Ser
305                 310                 315                 320

Asp Leu Ser Leu Cys Lys Ala Phe Asn Gln Asn His Pro Glu Ser Thr
                325                 330                 335

Ala Glu Phe Asn Asp Ser Asp Ser Gly Ile Ser Leu Asn Thr Ser Pro
            340                 345                 350

Ser Val Ala Ser Pro Glu His Ser Val Glu Ser Ser Tyr Gly Asp
        355                 360                 365

Thr Leu Leu Gly Leu Ser Asp Ser Glu Val Glu Glu Leu Asp Ser Ala
    370                 375                 380

Pro Gly Ser Val Lys Gln Asn Gly Pro Lys Thr Pro Val His Ser Ser
385                 390                 395                 400

Gly Asp Met Val Gln Pro Leu Ser Pro Ser Gln Gly Gln Ser Thr His
                405                 410                 415

Val His Asp Ala Gln Cys Glu Asn Thr Pro Glu Lys Glu Leu Pro Val
            420                 425                 430

Ser Pro Gly His Arg Lys Thr Pro Phe Thr Lys Asp Lys His Ser Ser
        435                 440                 445

Arg Leu Glu Ala His Leu Thr Arg Asp Glu Leu Arg Ala Lys Ala Leu
    450                 455                 460

His Ile Pro Phe Pro Val Glu Lys Ile Ile Asn Leu Pro Val Val Asp
465                 470                 475                 480

Phe Asn Glu Met Met Ser Lys Glu Gln Phe Asn Glu Ala Gln Leu Ala
                485                 490                 495
```

```
Leu Ile Arg Asp Ile Arg Arg Arg Gly Lys Asn Lys Val Ala Ala Gln
                500                 505                 510

Asn Cys Arg Lys Arg Lys Leu Glu Asn Ile Val Glu Leu Glu Gln Asp
        515                 520                 525

Leu Asp His Leu Lys Asp Glu Lys Glu Lys Leu Leu Lys Glu Lys Gly
        530                 535                 540

Glu Asn Asp Lys Ser Leu His Leu Leu Lys Lys Gln Leu Ser Thr Leu
545                 550                 555                 560

Tyr Leu Glu Val Phe Ser Met Leu Arg Asp Glu Asp Gly Lys Pro Tyr
                565                 570                 575

Ser Pro Ser Glu Tyr Ser Leu Gln Gln Thr Arg Asp Gly Asn Val Phe
            580                 585                 590

Leu Val Pro Lys Ser Lys Lys Pro
            595                 600

<210> SEQ ID NO 4
<211> LENGTH: 2859
<212> TYPE: DNA
<213> ORGANISM: Homo sapiens

<400> SEQUENCE: 4
aaatcaggga ggcgcagctc ctacaccaac gcctttccgg ggctccgggt gtgtttgttc    60
caactgttta aactgtttca aagcgtccga actccagcga ccttcgcaaa caactcttta   120
tctcgcgggc gagagcgctg cccttatttg cggggagggg caaactgaac gccggcaccg   180
gggagctaac ggagacctcc tctaggtccc ccgcctgctg ggaccccagc tggcagtccc   240
ttcccgcccc cggaccgcga gcttcttgcg tcagccccgg cgcgggtggg ggattttcgg   300
aagctcagcc cgcgcggccg gcggggggaag gaagggcccg gactcttgcc ccgcccttgt   360
ggggcgggag gcggagcggg gcaggggccc gccggcgtgt agccgattac cgagtgccgg   420
ggagcccgga ggagccgccg acgcagccgc caccgccgcc gccgccgcca ccagagccgc   480
cctgtccgcg ccgcgcctcg gcagccggaa cagggccgcc gtcggggagc ccaacacac    540 ggtccacagc tcatcatgat ggacttggag ctgccgccgc cggactccc gtcccagcag    600 gacatggatt tgattgacat actttggagg caagatatag atcttggagt aagtcgagaa   660
gtatttgact tcagtcagcg acggaaagag tatgagctgg aaaaacagaa aaaacttgaa   720
aaggaaagac aagaacaact ccaaaaggag caagagaaag cctttttcgc tcagttacaa   780
ctagatgaag agacaggtga atttctccca attcagccag cccagcacat ccagtcagaa   840
accagtggat ctgccaacta ctcccaggtt gcccacattc ccaaatcaga tgctttgtac   900
tttgatgact gcatgcagct tttggcgcag acattcccgt ttgtagatga caatgaggtt   960
tcttcggcta cgtttcagtc acttgttcct gatattcccg gtcacatcga gagcccagtc  1020
ttcattgcta ctaatcaggc tcagtcacct gaaacttctg ttgctcaggt agcccctgtt  1080
gatttagacg gtatgcaaca ggacattgag caagtttggg aggagctatt atccattcct  1140
gagttacagt gtcttaatat tgaaaatgac aagctggttg agactaccat ggttccaagt  1200
ccagaagcca aactgacaga agttgacaat tatcattttt actcatctat accctcaatg  1260
gaaaaagaag taggtaactg tagtccacat tttcttaatg cttttgagga ttccttcagc  1320
agcatcctct ccacagaaga ccccaaccag ttgacagtga actcattaaa ttcagatgcc  1380
acagtcaaca cagattttgg tgatgaattt tattctgctt tcatagctga gcccagtatc  1440
agcaacagca tgcccctcacc tgctactttta agccattcac tctctgaact tctaaatggg  1500
```

```
cccattgatg tttctgatct atcactttgc aaagctttca accaaaacca ccctgaaagc    1560
acagcagaat tcaatgattc tgactccggc atttcactaa acacaagtcc cagtgtggca    1620
tcaccagaac actcagtgga atcttccagc tatggagaca cactacttgg cctcagtgat    1680
tctgaagtgg aagagctaga tagtgcccct ggaagtgtca aacagaatgg tcctaaaaca    1740
ccagtacatt cttctgggga tatggtacaa cccttgtcac catctcaggg gcagagcact    1800
cacgtgcatg atgcccaatg tgagaacaca ccagagaaag aattgcctgt aagtcctggt    1860
catcggaaaa ccccattcac aaaagacaaa cattcaagcc gcttggaggc tcatctcaca    1920
agagatgaac ttagggcaaa agctctccat atcccattcc ctgtagaaaa aatcattaac    1980
ctccctgttg ttgacttcaa cgaaatgatg tccaaagagc agttcaatga agctcaactt    2040
gcattaattc gggatatacg taggaggggt aagaataaag tggctgctca gaattgcaga    2100 aaagaaaac tggaaaatat agtagaacta gagcaagatt tagatcattt gaaagatgaa    2160
aaagaaaaat tgctcaaaga aaaaggagaa aatgacaaaa gccttcaccct actgaaaaaa    2220 caactcagca ccttatatct cgaagttttc agcatgctac gtgatgaaga tggaaaacct    2280
tattctccta gtgaatactc cctgcagcaa acaagagatg gcaatgtttt ccttgttccc    2340
aaaagtaaga agccagatgt taagaaaaac tagatttagg aggatttgac cttttctgag    2400
ctagtttttt tgtactatta tactaaaagc tcctactgtg atgtgaaatg ctcatacttt    2460
ataagtaatt ctatgcaaaa tcatagccaa actagtata gaaaataata cgaaacttta    2520
aaaagcattg gagtgtcagt atgttgaatc agtagtttca ctttaactgt aaacaatttc    2580
ttaggacacc atttgggcta gtttctgtgt aagtgtaaat actacaaaaa cttatttata    2640
ctgttcttat gtcatttgtt atattcatag atttatatga tgatatgaca tctggctaaa    2700
aagaaattat tgcaaaacta accactatgt actttttttat aaatactgta tggacaaaaa    2760
atggcatttt ttatattaaa ttgtttagct ctggcaaaaa aaaaaatttt aagagctgg    2820 tactaataaa ggattattat gactgttaaa ttattaaaa                           2859
```

<210> SEQ ID NO 5
<211> LENGTH: 392
<212> TYPE: PRT
<213> ORGANISM: Homo sapiens

<400> SEQUENCE: 5

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
```

```
                130               135               140
Leu Trp Val Asp Ser Thr Pro Pro Gly Thr Arg Val Arg Ala Met
145               150               155               160

Ala Ile Tyr Lys Gln Ser Gln His Met Thr Glu Val Val Arg Cys
                165               170               175

Pro His His Glu Arg Cys Ser Asp Ser Asp Gly Leu Ala Pro Pro Gln
                180               185               190

His Leu Ile Arg Val Glu Gly Asn Leu Arg Val Glu Tyr Leu Asp Asp
                195               200               205

Arg Asn Thr Phe Arg His Ser Val Val Pro Tyr Glu Pro Pro Glu
210               215               220

Val Gly Ser Asp Cys Thr Thr Ile His Tyr Asn Tyr Met Cys Asn Ser
225               230               235               240

Ser Cys Met Gly Gly Met Asn Arg Arg Pro Ile Leu Thr Ile Ile Thr
                245               250               255

Leu Glu Asp Ser Ser Gly Asn Leu Leu Gly Arg Asn Ser Phe Glu Val
                260               265               270

Arg Val Cys Ala Cys Pro Gly Arg Asp Arg Arg Thr Glu Glu Glu Asn
                275               280               285

Leu Arg Lys Lys Gly Glu Pro His His Glu Leu Pro Pro Gly Ser Thr
290               295               300

Lys Arg Ala Leu Pro Asn Asn Thr Ser Ser Ser Pro Gln Pro Lys Lys
305               310               315               320

Lys Pro Leu Asp Gly Glu Tyr Phe Thr Leu Gln Ile Arg Gly Arg Glu
                325               330               335

Arg Phe Glu Met Phe Arg Glu Leu Asn Glu Ala Leu Glu Leu Lys Asp
                340               345               350

Ala Gln Ala Gly Lys Glu Pro Gly Gly Ser Arg Ala His Ser Ser His
                355               360               365

Leu Lys Ser Lys Lys Gly Gln Ser Thr Ser Arg His Lys Lys Leu Met
                370               375               380

Phe Lys Thr Glu Gly Pro Asp Ser
385               390

<210> SEQ ID NO 6
<211> LENGTH: 2591
<212> TYPE: DNA
<213> ORGANISM: Homo sapiens

<400> SEQUENCE: 6
gatgggattg gggttttccc ctcccatgtg ctcaagactg gcgctaaaag ttttgagctt    60
ctcaaaagtc tagagccacc gtccagggag caggtagctg ctgggctccg ggacacttt    120 gcgttcgggc tgggagcgtg cttccacga cggtgacacg cttccctgga ttggcagcca    180
gactgccttc cggtcactg ccatggagga gccgcagtca gatcctagcg tcgagccccc    240
tctgagtcag gaaacatttt cagacctatg gaaactactt cctgaaaaca acgttctgtc    300 cccttgccg tcccaagcaa tggatgattt gatgctgtcc ccggacgata ttgaacaatg    360
gttcactgaa gacccaggtc agatgaagc tcccagaatg ccagaggctg ctccccccgt    420
ggcccctgca ccagcagctc ctacaccggc ggccctgca ccagccccct cctggcccct    480
gtcatcttct gtcccttccc agaaaaccta ccagggcagc tacggtttcc gtctgggctt    540
cttgcattct gggacagcca agtctgtgac ttgcacgtac tcccctgccc tcaacaagat    600
gttttgccaa ctggccaaga cctgccctgt gcagctgtgg gttgattcca caccccgcc    660
```

-continued

```
cggcacccgc gtccgcgcca tggccatcta caagcagtca cagcacatga cggaggttgt    720
gaggcgctgc ccccaccatg agcgctgctc agatagcgat ggtctggccc ctcctcagca    780
tcttatccga gtggaaggaa atttgcgtgt ggagtatttg gatgacagaa acacttttcg    840
acatagtgtg gtggtgccct atgagccgcc tgaggttggc tctgactgta ccaccatcca    900
ctacaactac atgtgtaaca gttcctgcat gggcggcatg aaccggaggc ccatcctcac    960
catcatcaca ctggaagact ccagtggtaa tctactggga cggaacagct ttgaggtgcg   1020
tgtttgtgcc tgtcctggga gagaccggcg cacagaggaa gagaatctcc gcaagaaagg   1080
ggagcctcac cacgagctgc ccccaggag cactaagcga gcactgccca acaacaccag    1140
ctcctctccc cagccaaaga agaaaccact ggatggagaa tatttcaccc ttcagatccg   1200
tgggcgtgag cgcttcgaga tgttccgaga gctgaatgag gccttggaac tcaaggatgc   1260
ccaggctggg aaggagccag gggggagcag ggctcactcc agccacctga agtccaaaaa   1320
gggtcagtct acctcccgcc ataaaaaact catgttcaag acagaagggc ctgactcaga   1380
ctgacattct ccacttcttg ttccccactg acagcctccc accccatct ctccctcccc    1440
tgccattttg ggttttgggt ctttgaaccc ttgcttgcaa taggtgtgcg tcagaagcac   1500
ccaggacttc catttgcttt gtcccggggc tccactgaac aagttggcct gcactggtgt   1560
tttgttgtgg ggaggaggat ggggagtagg acataccagc ttagatttta aggtttttac   1620
tgtgagggat gtttgggaga tgtaagaaat gttcttgcag ttaagggtta gtttacaatc   1680
agccacattc taggtagggg cccacttcac cgtactaacc agggaagctg tccctcactg   1740
ttgaattttc tctaacttca aggcccatat ctgtgaaatg ctggcatttg cacctacctc   1800
acagagtgca ttgtgagggt taatgaaata atgtacatct ggccttgaaa ccacctttta   1860
ttacatgggg tctagaactt gacccccttg agggtgcttg ttccctctcc ctgttggtcg   1920
gtgggttggt agtttctaca gttgggcagc tggttaggta gagggagttg tcaagtctct   1980
gctggcccag ccaaaccctg tctgacaacc tcttggtgaa ccttagtacc taaaaggaaa   2040
tctcacccca tcccacaccc tggaggattt catctcttgt atatgatgat ctggatccac   2100
caagacttgt tttatgctca gggtcaattt ctttttttctt tttttttttt tttttctttt  2160
ttctttgaga ctgggtctcg ctttgttgcc caggctggag tggagtggcg tgatcttggc   2220
ttactgcagc ctttgcctcc ccggctcgag cagtcctgcc tcagcctccg gagtagctgg   2280
gaccacaggt tcatgccacc atggccagcc aacttttgca tgttttgtag agatggggtc   2340
tcacagtgtt gcccaggctg gtctcaaact cctgggctca ggcgatccac ctgtctcagc   2400
ctcccagagt gctgggatta caattgtgag ccaccacgtc cagctggaag ggtcaacatc   2460
ttttacattc tgcaagcaca tctgcatttt caccccaccc ttcccctcct tctcccttt    2520
tatatcccat tttatatcg atctcttatt ttacaataaa actttgctgc cacctgtgtg   2580
tctgaggggt g                                                        2591
```

COMPOSITIONS AND METHODS FOR SENSITIZING A NEOPLASTIC CELL TO RADIATION

CROSS REFERENCE TO RELATED APPLICATIONS

This application is a U.S. utility application under 37 CFR 1.53(b), which claims priority to and the benefit of U.S. Provisional Application No. 61/868,906, which was filed on Aug. 22, 2013, which is incorporated herein by this reference.

STATEMENT OF RIGHTS TO INVENTIONS MADE UNDER FEDERALLY SPONSORED RESEARCH

This work was supported by the following grants from the National Institutes of Health, Grant Nos: NCI RO1 CA109038, K08 CA163677, NIH RC2 CA138399-01, and GM38627. The government has certain rights in the invention.

SEQUENCE LISTING

The instant application contains a Sequence Listing which has been submitted electronically in ASCII format and is hereby incorporated by reference in its entirety. Said ASCII copy, created on Sep. 18, 2014, is named 364950-1001US1 (00026)_SL.txt and is 16,701 bytes in size.

BACKGROUND OF THE INVENTION

Radiation, alone or in combination with chemotherapy, is a mainstay of treatment for many solid malignancies. For example, patients with nonresectable non-small cell lung cancer receive radiotherapy. Currently, only 12-15% of such patients survive. There is an urgent need for agents that can be used in combination with radiotherapy to sensitize cancer cells to radiation.

SUMMARY OF THE INVENTION

As described below, the present invention provides for the use of radiation sensitizing agents in combination with radiation for the treatment of neoplasia, methods for the identification of genotype-specific radiation sensitizing agents, and methods of identifying patients who could benefit from therapy with a genotype-specific radiation sensitizing agent.

In one aspect, the invention generally features a method of sensitizing a neoplastic cell (e.g., non-small cell lung cancer cell) to radiation, the method involves contacting the cell with a PI3 kinase inhibitor and exposing the cell to radiation, thereby sensitizing the cell to radiation.

In another aspect, the invention features a method of enhancing cell death or reducing proliferation in a neoplastic cell (e.g., non-small cell lung cancer cell), the method involves contacting the cell with a PI3 kinase inhibitor and exposing the cell to radiation, thereby enhancing cell death or reducing proliferation in the neoplastic cell.

In yet another aspect, the method of enhancing radiation sensitivity in a subject (e.g., human) having a radiation-resistant neoplasia, the method involves administering to the subject radiation and a PI3 kinase inhibitor, thereby enhancing the subject's sensitivity to radiation.

In still another aspect, the invention features a method of treating a subject with non-small cell lung cancer, the method involves characterizing the radiation-susceptibility of the non-small cell lung cancer by detecting a TP53 or NFE2L2 mutation in the subject; and administering to the subject radiation and a PI3 kinase inhibitor, thereby enhancing the subject's sensitivity to radiation.

In yet another aspect, high-throughput clonogenic growth assay, the method involves automatedly plating neoplastic cells into a plate having between 100 and 500 wells; contacting the cells with a candidate agent prior to, during, or after radiation exposure; and assaying cell proliferation between 7-21 days following plating. In one embodiment, the plating density of the cells is increased or decreased. In another embodiment, the cell proliferation assay is carried 9 days following contact with the candidate agent.

In various embodiments of any of the above aspects, the radiation-susceptibility of the neoplasia or subject is characterized (e.g., by assaying for NRF2 activation or TP53 activation) prior to, during, or following administration of radiation. In other embodiments of the above aspects, radiation resistance is characterized by detecting a TP53 mutation in the subject, where a TP53 missense mutation identifies the neoplasia as radiation resistant and a TP53 disruptive mutation identifies the neoplasia as radiation sensitive. In other embodiments of the above aspects, the radiation susceptibility is characterized by assaying (e.g., sequencing) a TP53 DNA binding domain (aa. 101-305) for mutations. In still other embodiments, the radiation susceptibility is characterized by detecting a TP53 mutation selected from the group consisting of W146*, E171*, Q167*, E298*, V143A, D259V, R249S, M237I, V272M, V143M, R248W, and R158G Intron (ins). In still other embodiments of the above aspects, radiation resistance is characterized by detecting a NFE2L2 mutation associated with radiation resistance. In particular, embodiments, the NFE2L2 mutation is D77V, P128L, E79K, or del 16-34. In still other embodiments, the PI3 kinase inhibitor is a PI3K alpha selective inhibitor. In particular, the PI3 kinase inhibitor is LY 294002 or NVP-BKM120. In still other embodiments of the above aspects, the agent is an inhibitory nucleic acid that reduces NRF2 expression (e.g., a NRF2-1 shRNA, AGAGCAAGATTTA-GATCATTT (SEQ ID NO: 1) and/or NRF2-2 shRNA, GCTCCTACTGTGATGTGAAAT (SEQ ID NO: 2)). In still other embodiments of the above aspects, the PI3 kinase inhibitor reduces NRF2-mediated transcription. In still other embodiments of the above aspects, radiation resistance is characterized by detecting a TP53 mutation in the cancer, where a TP53 missense mutation identifies the cancer as radiation resistant and a TP53 disruptive mutation identifies the cancer as radiation sensitive.

Compositions and articles defined by the invention were isolated or otherwise manufactured in connection with the examples provided below. Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "NUCLEAR FACTOR ERYTHROID 2-LIKE 2 (NFE2L2)" is meant a human gene encoding NFE2-related Factor 2 (NRF2).

By "NRF2 polypeptide" is meant a protein or fragment thereof having at least about 85% amino acid identity to UniProt identifier Q16236 and having transcriptional regulatory and/or DNA binding activity. An exemplary NRF2 amino acid sequence is provided below (SEQ ID NO: 3):

```
sp|Q16236|NF2L2_HUMAN Nuclear factor erythroid 2-related factor 2
OS = Homo sapiens GN = NFE2L2 PE = 1 SV = 3
         10         20         30         40         50         60
    MMDLELPPPG LPSQQDMDLI DILWRQDIDL GVSREVFDFS QRRKEYELEK QKKLEKERQE 70         80         90        100        110        120
    QLQKEQEKAF FAQLQLDEET GEFLPIQPAQ HIQSETSGSA NYSQVAHIPK SDALYFDDCM 130        140        150        160        170        180
    QLLAQTFPFV DDNEVSSATF QSLVPDIPGH IESPVFIATN QAQSPETSVA QVAPVDLDGM 190        200        210        220        230        240
    QQDIEQVWEE LLSIPELQCL NIENDKLVET TMVPSPEAKL TEVDNYHFYS SIPSMEKEVG 250        260        270        280        290        300
    NCSPHFLNAF EDSFSSILST EDPNQLTVNS LNSDATVNTD FGDEFYSAFI AEPSISNSMP 310        320        330        340        350        360
    SPATLSHSLS ELLNGPIDVS DLSLCKAFNQ NHPESTAEFN DSDSGISLNT SPSVASPEHS 370        380        390        400        410        420
    VESSSYGDTL LGLSDSEVEE LDSAPGSVKQ NGPKTPVHSS GDMVQPLSPS QGQSTHVHDA 430        440        450        460        470        480
    QCENTPEKEL PVSPGHRKTP FTKDKHSSRL EAHLTRDELR AKALHIPFPV EKIINLPVVD 490        500        510        520        530        540
    FNEMMSKEQF NEAQLALIRD IRRRGKNKVA AQNCRKRKLE NIVELEQDLD HLKDEKEKLL 550        560        570        580        590        600
    KEKGENDKSL HLLKKQLSTL YLEVFSMLRD EDGKPYSPSE YSLQQTRDGN VFLVPKSKKP
```

By "NRF2 polynucleotide" is meant a nucleic acid sequence encoding an NRF2 polypeptide. An exemplary sequence is provided at NCBI Ref: NM_006164.4 below (SEQ ID NO: 4):

```
   1 aaatcaggga ggcgcagctc ctacaccaac gcctttccgg ggctccgggt gtgtttgttc   61 caactgttta aactgtttca aagcgtccga actccagcga ccttcgcaaa caactctttta 121 tctcgcgggc gagagcgctg cccttatttg cggggggaggg caaactgaac gccggcaccg 181 gggagctaac ggagacctcc tctaggtccc ccgcctgctg gaccccagc tggcagtccc  241 ttcccgcccc cggaccgcga gcttcttgcg tcagccccgg cgcgggtggg ggattttcgg  301 aagctcagcc cgcgcggccg gcggggggaag gaagggcccg gactcttgcc ccgcccttgt  361 ggggcgggag gcggagcggg gcaggggccc gccggcgtgt agccgattac cgagtgccgg  421 ggagcccgga ggagccgccg acgcagccgc caccgccgcc gccgccgcca ccagagccgc  481 cctgtccgcg ccgcgcctcg gcagccggaa cagggccgcc gtcgggggagc cccaacacac  541 ggtccacagc tcatcatgat ggacttggag ctgccgccgc cgggactccc gtcccagcag  601 gacatggatt tgattgacat actttggagg caagatatag atcttggagt aagtcgagaa  661 gtatttgact tcagtcagcg acggaaagag tatgagctgg aaaaacagaa aaaacttgaa  721 aaggaaagac aagaacaact ccaaaaggag caagagaaag cctttttcgc tcagttacaa  781 ctagatgaag agacaggtga attttctccca attcagccaa cccagcacat ccagtcagaa  841 accagtggat ctgccaacta ctcccaggtt gcccacattc ccaaatcaga tgctttgtac  901 tttgatgact gcatgcagct tttggcgcag acattcccgt ttgtagatga caatgaggtt  961 tcttcggcta cgtttcagtc acttgttcct gatattcccg gtcacatcga gagcccagtc 1021
```

```
ttcattgcta ctaatcaggc tcagtcacct gaaacttctg ttgctcaggt agccctgtt  1081 gatttagacg gtatgcaaca ggacattgag caagtttggg aggagctatt atccattcct 1141 gagttacagt gtcttaatat tgaaaatgac aagctggttg agactaccat ggttccaagt 1201 ccagaagcca aactgacaga agttgacaat tatcattttt actcatctat accctcaatg 1261 gaaaagaag taggtaactg tagtccacat tttcttaatg cttttgagga ttccttcagc 1321 agcatcctct ccacagaaga ccccaaccag ttgacagtga actcattaaa ttcagatgcc 1381 acagtcaaca cagattttgg tgatgaattt tattctgctt tcatagctga gcccagtatc 1441 agcaacagca tgccctcacc tgctacttta agccattcac tctctgaact tctaaatggg 1501 cccattgatg tttctgatct atcactttgc aaagcttttca accaaaacca ccctgaaagc 1561 acagcagaat tcaatgattc tgactccggc atttcactaa acacaagtcc cagtgtggca 1621 tcaccagaac actcagtgga atcttccagc tatggagaca cactacttgg cctcagtgat 1681 tctgaagtgg aagagctaga tagtgccct ggaagtgtca acagaatgg tcctaaaaca 1741 ccagtacatt cttctgggga tatggtacaa cccttgtcac catctcaggg gcagagcact 1801 cacgtgcatg atgcccaatg tgagaacaca ccagagaaag aattgcctgt aagtcctggt 1861 catcggaaaa ccccattcac aaaagacaaa cattcaagcc gcttggaggc tcatctcaca 1921 agagatgaac ttagggcaaa agctctccat atcccattcc ctgtagaaaa aatcattaac 1981 ctccctgttg ttgacttcaa cgaaatgatg tccaaagagc agttcaatga agctcaactt 2041 gcattaattc gggatatacg taggaggggt aagaataaag tggctgctca gaattgcaga 2101 aaagaaaac tggaaaatat agtagaacta gagcaagatt tagatcattt gaaagatgaa 2161 aaagaaaat tgctcaaaga aaaaggagaa aatgacaaaa gccttcacct actgaaaaaa 2221 caactcagca cctatatct cgaagttttc agcatgctac gtgatgaaga tggaaaacct 2281 tattctccta gtgaatactc cctgcagcaa acaagagatg gcaatgtttt ccttgttccc 2341 aaaagtaaga agccagatgt taagaaaaac tagatttagg aggatttgac ctttttctgag 2401 ctagtttttt tgtactatta tactaaaagc tcctactgtg atgtgaaatg ctcatacttt 2461 ataagtaatt ctatgcaaaa tcatagccaa aactagtata gaaataata cgaaacttta 2521 aaaagcattg gagtgtcagt atgttgaatc agtagtttca ctttaactgt aaacaatttc 2581 ttaggacacc atttgggcta gtttctgtgt aagtgtaaat actacaaaaa cttatttata 2641 ctgttcttat gtcatttgtt atattcatag atttatatga tgatatgaca tctggctaaa 2701 aagaaattat tgcaaaacta accactatgt acttttttat aaatactgta tggacaaaaa 2761 atggcatttt ttatattaaa ttgtttagct ctggcaaaaa aaaaaatttt taagagctgg 2821 tactaataaa ggattattat gactgttaaa ttattaaaa
```

By "TP53 polypeptide" is meant a protein or fragment thereof having at least 85% amino acid identity to NP_000537.3 and having DNA binding or transcriptional regulatory activity. An exemplary TP53 amino acid sequence is provided below (SEQ ID NO: 5):

MEEPQSDPSVEPPLSQETFSDLWKLLPENNVLSPLPSQAMDDLM

LSPDDIEQWFTEDPGPDEAPRMPEAAPPVAPAPAAPTPAAPAPAPSWPL

SSSVPSQKTYQGSYGFRLGFLHSGTAKSVTCTYSPALNKMFCQLAKTCP

VQLWVDSTPPPGTRVRAMAIYKQSQHMTEVVRRCPHHERCSDSDGLAPP

QHLIRVEGNLRVEYLDDRNTFRHSVVVPYEPPEVGSDCTTIHYNYMCNS

SCMGGMNRRPILTIITLEDSSGNLLGRNSFEVRVCACPGRDRRTEEENL

RKKGEPHHELPPGSTKRALPNNTSSSPQPKKKPLDGEYFTLQIRGRERF

EMFRELNEALELKDAQAGKEPGGSRAHSSHLKSKKGQSTSRHKKLMFKT

EGPDS

By "TP53 polynucleotide" is meant a nucleic acid sequence that encodes a TP53 polypeptide. An exemplary TP53 polynucleotide sequence is provided at NM_000546.5 (SEQ ID NO: 6):

```
  1 gatgggattg gggttttccc ctcccatgtg ctcaagactg gcgctaaaag ttttgagctt   61
    ctcaaaagtc tagagccacc gtccagggag caggtagctg ctgggctccg ggacacttt   121
    gcgttcgggc tgggagcgtg cttccacga cggtgacacg cttccctgga ttggcagcca   181
    gactgccttc cgggtcactg ccatggagga gccgcagtca gatcctagcg tcgagccccc   241
    tctgagtcag gaaacatttt cagacctatg gaaactactt cctgaaaaca acgttctgtc   301
    ccccttgccg tcccaagcaa tggatgattt gatgctgtcc ccggacgata ttgaacaatg   361
    gttcactgaa gacccaggtc cagatgaagc tcccagaatg ccagaggctg ctcccccgt   421
    ggccctgca ccagcagctc ctacaccggc ggccctgca ccagccccct cctggccct    481
    gtcatcttct gtcccttccc agaaaaccta ccagggcagc tacggtttcc gtctgggctt   541
    cttgcattct gggacagcca agtctgtgac ttgcacgtac tccctgccc tcaacaagat   601
    gttttgccaa ctggccaaga cctgcccgt gcagctgtgg gttgattcca cacccccgcc   661
    cggcacccgc gtccgcgcca tggccatcta caagcagtca cagcacatga cggaggttgt   721
    gaggcgctgc ccccaccatg agcgctgctc agatagcgat ggtctggccc ctcctcagca   781
    tcttatccga gtggaaggaa atttgcgtgt ggagtatttg gatgacagaa acacttttcg   841
    acatagtgtg gtggtgccct atgagccgcc tgaggttggc tctgactgta ccaccatcca   901
    ctacaactac atgtgtaaca gttcctgcat gggcggcatg aaccggaggc ccatcctcac   961
    catcatcaca ctggaagact ccagtggtaa tctactggga cggaacagct ttgaggtgcg  1021
    tgtttgtgcc tgtcctggga gagaccggcg cacagaggaa gagaatctcc gcaagaaagg  1081
    ggagcctcac cacgagctgc ccccaggag cactaagcga gcactgccca acaacaccag   1141
    ctcctctccc cagccaaaga gaaaccact ggatggagaa tatttcaccc ttcagatccg  1201
    tgggcgtgag cgcttcgaga tgttccgaga gctgaatgag gccttggaac tcaaggatgc  1261
    ccaggctggg aaggagccag gggggagcag ggctcactcc agccacctga gtccaaaaa  1321
    gggtcagtct acctcccgcc ataaaaaact catgttcaag acagaagggc ctgactcaga  1381
    ctgacattct ccacttcttg ttccccactg acagcctccc accccatct ctccctcccc   1441
    tgccattttg ggttttgggt ctttgaaccc ttgcttgcaa taggtgtgcg tcagaagcac   1501
    ccaggacttc catttgcttt gtcccggggc tccactgaac aagttggcct gcactggtgt   1561
    tttgttgtgg ggaggaggat ggggagtagg acataccagc ttagatttta aggttttac   1621
    tgtgagggat gtttgggaga tgtaagaaat gttcttgcag ttaagggtta gtttacaatc  1681
    agccacattc taggtagggg cccacttcac cgtactaacc agggaagctg tccctcactg   1741
    ttgaattttc tctaacttca aggcccatat ctgtgaaatg ctggcatttg cacctacctc  1801
    acagagtgca ttgtgagggt taatgaaata atgtacatct ggccttgaaa ccaccttta   1861
    ttacatgggg tctagaactt gaccccttg agggtgcttg ttccctctcc ctgttggtcg  1921
    gtgggttggt agtttctaca gttgggcagc tggttaggta gagggagttg tcaagtctct  1981
    gctggcccag ccaaaccctg tctgacaacc tcttggtgaa ccttagtacc taaaaggaaa  2041
    tctcacccca tccacaccc tggaggattt catctcttgt atatgatgat ctggatccac   2101
    caagacttgt tttatgctca gggtcaattt cttttttctt tttttttttt ttttttcttt   2161
    ttctttgaga ctgggtctcg ctttgttgcc caggctggag tggagtggcg tgatcttggc   2221
    ttactgcagc ctttgcctcc ccggctcgag cagtcctgcc tcagcctccg gagtagctgg   2281
    gaccacaggt tcatgccacc atggccagcc aacttttgca tgttttgtag agatggggtc   2341
    tcacagtgtt gccaggctg gtctcaaact cctgggctca ggcgatccac ctgtctcagc   2401
    ctcccagagt gctgggatta caattgtgag ccaccacgtc cagctggaag ggtcaacatc  2461
```

```
                                                            -continued
ttttacattc tgcaagcaca tctgcatttt cacccacc  ttccctcct  tctcccttt   2521 tatatcccat  ttttatatcg atctcttat  ttacaataaa actttgctgc cacctgtgtg 2581 tctgaggggt g
```

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include non-small cell lung cancer and other neoplasias.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1, Panel (a) is a graph that shows results of a clonogenic assay of H520, LC-1/SQ-SF, and LUDLU-1 after exposure to 0, 2, 5, or 8 Gy of γ-rays. Data represents the mean of n≥2 for each cell line. FIG. 1, Panel (b) is a micrograph that shows results of a clonogenic assay of cell line HARA performed in a 6-well plate after exposure to 0, 2, 5, or 8 Gy of γ-rays. FIG. 1, Panel (c) is a graph that shows the surviving fraction as a function of dose for HARA after exposure to 0, 2, 5, or 8 Gy of γ-rays (*=biological duplicate). Data are expressed as the means±s.d.

FIG. 2, Panel (a) provides graphs showing an idealized sigmoidal curve extrapolated from primary data demonstrating the dependence of growth (RLU) on cell density (top). Growth as a function of cell number per well is demonstrated for cell lines LUDLU-1 (middle) and EBC-1 (bottom) after 9 days of growth. FIG. 2, Panel (b) provides graphs showing the proliferation of LUDLU-1 and EBC-1 after exposure to 0, 1, 2, 4, or 6 Gy of γ-rays is plotted as a function of time. Radiation exposure occurred on day 0 and measurements of proliferation were taken at 4, 6, 8, and 9 days. FIG. 2, Panel (c) provides light microscopy images of LUDLU-1 and EBC-1 that were taken on day 9 from control (no irradiation) wells in a 384-plate from the same experiment depicted in (b). FIG. 2, Panel (d) is a graph that shows the proliferation fraction as a function of dose for LUDLU-1 and EBC-1 after exposure to γ-rays (*=biological duplicates). Data are expressed as the means±s.d and are representative of ≥2 experiments.

FIG. 3, Panel (a) is a table that (Top) shows $R^2$ values, calculated by comparing the proliferating fraction PFx from high-throughput profiling and SFx from clonogenic assay. $R^2$ values depicted in red if P<0.05. (Bottom) Scatter plots and linear regression for PF4 with SF2, SF5, or SF8. FIG. 3, Panel (b) is a graph showing that integral survival was calculated for each cell line, n≥2). Error bars represent SEM. FIG. 3, Panel (c) provides plots showing that integral survival was calculated for proliferation assays for each cell line at days 4, 6, 8, and 9. Separately, integral survival was calculated for clonogenic survival assay. Data represents the average integral survival value for each cell line, n≥2.

FIG. 5, Panel (a) is a graph showing NRF2 scores from lung SqCC cell lines and integral survival were plotted. FIG. 5, Panel (b) is a graph that shows the average integral survival values calculated from high-throughput assays were plotted as function of high NRF2 score defined as greater than the median (0.10) and/or the presence of alteration in the coding region of NFE2L2 or KEAP1. FIG. 5, Panel (c) shows a schematic depiction of the functional domains of NRF2. The Neh2 domain contains the two KEAP1 association motifs, DLG and ETGE. FIG. 5, Panel (d) is an immunoblot that shows NRF2 protein level in cell lines: RERF-LC-AI (−/+ tBHQ), LC-1/SQSF, and HCC15; Actin was used as a loading control. Immunblot analysis of NRF2 protein in LC-1/SQ-SF (FIG. 5, Panel (e)) and RERF-LC-AI (FIG. 5, Panel (h)) cells infected with control shRNA (shNTC) and shNRF2-1 and shNRF2-2 after induction with Doxycycline for 24 hours; Actin was used as a loading control. FIG. 5, Panels (f), (i), (g), and are graphs. LC-1/SQSF (FIG. 5, Panel (f)) and RERF-LC-AI (i) clones infected with shNTC, shNRF2-1, or shNRF2-2 were measured for clonogenic survival after induction with Doxycycline. LC-1/SQSF clones infected with shNTC or shNRF2-1 (FIG. 5, Panel (g)) and RERF-LC-AI clones infected with shNTC, shNRF2-1, or shNRF2-2 (FIG. 5, Panel (j)) were treated as control (0 Gy) or with radiation (2, 4, 6 Gy) after induction with Doxycycline for 24 hours. Data points represent mean values of duplicates (clonogenic survival) or six replicates (clonogenic survival after radiation) and are representative of three independent experiments. Error bars represent SEM. Cropped blots were imported directly into Adobe Illustrator CS6; no adjustments of brightness, contrast, or color balance were applied.

FIG. 6, Panel (a) is a scatter plot of NRF2 signature score for 967 cell lines in the CCLE stratified by disease site and histology where appropriate. Solid bars represent the mean in each category. Dashed line represents the median across all CCLE lines. The top five tumor types by mean NRF2 score were liver (0.19), lung SqCC (0.17), biliary tract (0.16), kidney (0.16), and esophageal cancer (0.15). FIG. 6, Panel (b) is a scatter plot of NRF2 signature score for cell lines derived from lung stratified by histology. Solid bars represent the mean in each category. Dashed line represents the median for all CCLE lines.

FIG. 7, Panel (a) is a Table showing the rank, cmap name, connectivity score for each of the selected chemicals is shown. FIG. 7, Panel (b) shows that a "barview" is constructed from horizontal lines, each representing an individual treatment instance, ordered by their corresponding connectivity scores with the NFE2L2 signature (+1, top; −1, bottom). All instances in the data set are colored in black. Colors applied to the remaining instances reflect the sign of their scores (green, positive; gray, null; red, negative). FIG. 7, Panel (b) shows that LC-1/SQSF clones containing the ARE luciferase reporter were treated with LY 294002, NVP-BKM 120, and TGX-221 for 24 hours. FIG. 7, Panel (c) provides 2 graphs showing NRF2 activity and cellular viability. Cellular viability was measured at 48 hours. Data points represent mean values of triplicates and error bars represent SD. The experiment was performed three times with comparable results. FIG. 7, Panel (d) shows that the pan-PI3K inhibitor NVP-BKM 120 decreases NRF2 protein level. LC-1/SQSF cells were treated with control (DMSO), LY 294002, NVP-BKM 120, or TGX-221 and HCC15 cells were treated with DMSO and NVP-BKM120 for 24 hours and lysates were subjected to immunoblot analysis for the NRF2 protein. RERF-LC-AI cells were treated with DMSO and NVP-BKM120 for 24 hours followed by induction with 10 μM tBHQ for 24 hours before lysates were subjected to immunoblot analysis for the NRF2 protein. Actin was used as a loading control. Cropped blots were imported directly into Adobe Illustrator CS6; no adjustments of brightness, contrast, or color balance were applied.

FIG. 8, Panel (a) provides 5 graphs. RERF-LC-AI, SQ-1, LC-1/SQSF, HCC15, or A549 cells were incubated with NVP-BKM120 for 24 hours and treated as control (0 Gy) or with radiation. Survival is measured by clonogenic assay. Data points represent mean values of duplicates and error bars represent SD. The experiment was performed three times with comparable results. In the experiment shown in Panel (a), surviving fraction after exposure to 2 and 4 Gy (RERF-LC-AI, LC-1/SQSF, and HCC-15), 4 and 6 Gy (A549), and 1 and 2 Gy (SQ-1) radiation for cells incubated with DMSO alone are as follows: LC-1/SQSF, 0.71±0.11 and 0.37±0.08; HCC15, 0.75±0.9 and 0.42±0.12; RERF-LC-AI, 0.52±0.06 and 0.33±0.01; A549, 0.46±0.09 and 0.24±0.06; SQ-1, 0.65±0.16 and 0.48±0.06. FIG. 8, Panel (b) shows the NFE2L2/KEAP1 genotype of cell lines tested for radiosensitization

FIG. 11, Panel (a) shows that TP53 is not significantly expressed in cell lines with disruptive mutations. TP53 mRNA levels (see Methods) were plotted as a function of genotype. FIG. 11, Panel (b) shows that non-disruptive mutations in TP53 confer radiation resistance. Integral survival calculated from high-throughput platform were plotted as function of TP53 genotype. FIG. 11, Panels (c) and (d) show that TP53 mRNA level positively correlates with radiation resistance. Integral survival calculated from clonogenic assay (FIG. 11, Panel (c)) and high-throughput platform (FIG. 11, Panel (d)) were plotted as a function of TP53 mRNA level. FIG. 11, Panel (e) TP53 activity correlates with radiation resistance. TP53 signature score (see Methods) and integral survival calculated from high-throughput platform were plotted. Data represents the average integral survival value for each cell line, n≥2. $R^2$ was calculated from the Pearson correlation coefficient. P represents a two-tailed value. $P<0.05$ was considered statistically significant (*).

DETAILED DESCRIPTION OF THE INVENTION

Figure 1:
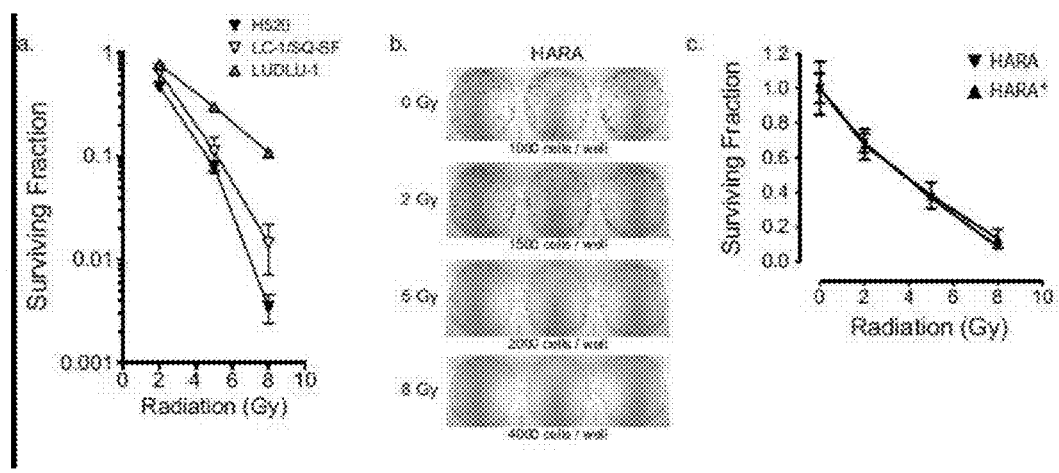
FIG. 1 shows clonogenic survival following exposure to γ-radiation.

The invention features the use of a genotype-selective radiation sensitizing agent in combination with radiation for the treatment of neoplasia, methods of identifying radiation sensitizing agents, and methods for identifying patients that could benefit from treatment with a a genotype-selective radiation sensitizing agent.

The invention is based, at least in part, on the discovery that the PI3K inhibitor, NVP-BKM120, decreased NRF2 protein levels and sensitized NFE2L2 or KEAP1 mutant cells to radiation. Radiation therapy is one of the mainstays of anti-cancer treatment, but the relationship between the radiosensitivity of cancer cells and their genomic characteristics is still not well-defined. As reported in more detail below, the invention provides a high-throughput platform for measuring radiation survival in vitro and its validation by comparison to conventional clonogenic radiation survival analysis. Results from this high-throughput assay were combined with genomic parameters in cell lines from squamous cell lung carcinoma, which is typically treated by radiation therapy, to identify parameters that predict radiation sensitivity. In particular, activation of NFE2L2, a frequent event in lung squamous cancers, confers radiation resistance. An expression-based, in silico screen identified inhibitors of PI3K as NFE2L2 antagonists. The selective PI3K inhibitor, NVP-BKM120, both decreased NRF2 protein levels and sensitized NFE2L2 or KEAP1 mutant cells to radiation. Results from this high-throughput assay were combined with single-sample gene set enrichment analysis (ssGSEA) of gene expression data. The resulting analysis identified pathways implicated in cell survival, genotoxic stress, detoxification, and innate and adaptive immunity, as key correlates of radiation sensitivity. The integrative, high-throughput methods shown here for large-scale profiling of radiation survival and genomic features of solid-tumor derived cell lines should facilitate tumor radiogenomics and the discovery of genotype-selective radiation sensitizers and protective agents.

Chemoradiation

The use of a combination of radiation and chemotherapy, or chemoradiation, is the mainstay of treatment for many solid malignancies (1). In recent years, the use of cancer chemotherapeutic drugs has increasingly been driven by genomic characteristics, especially for targeted therapies (2-4). In contrast, despite correlative studies that have established gene classifiers predictive of radiation response across the NCI-60 panel of cell lines (5-7), there have not been extensive systematic analyses of the correlation between radiation sensitivity and genomic parameters.

In 1956, Puck and Marcus described a technique for assessment of clonogenic growth of HeLa cells after exposure to radiation in vitro (8). The clonogenic assay is still widely considered the most reliable in vitro assay for assessing toxicity in cell lines, measuring the sum of all modes of cell death while simultaneously accounting for delayed growth arrest. Unlike cellular response to cytotoxic compounds, most cells lethally damaged by radiation do not immediately cease proliferation but may multiply for several generations before terminating reproduction (9). Therefore, short-term assays that are useful for the study of cytotoxic compounds have not proven effective in accurately profiling solid-tumor derived cell survival after exposure to radiation.

Although several high-throughput screening assays that measure cellular response to DNA double-strand breaks have been used effectively to identify modulators of DNA damage response (DDR) (10, 11), such pathway-focused assays lack the scope needed for a comprehensive evaluation of the physiological and genomic parameters influencing survival following exposure to radiation. The lack of a high-throughput assay measuring clonogenic survival has been a major obstacle in radiobiology research. Such an assay could facilitate large-scale studies to identify predictive markers for tumor response to therapy and facilitate development of rational combinatorial (chemoradiation) treatment. Several radiosensitizing drugs are currently used clinically, but despite their demonstrated efficacy they have numerous shortcomings (12, 13). In particular, their efficacy and toxicity is likely to vary based on the genetic characteristics of individual tumors, significantly limiting their optimal use. Recent studies have identified frequent and targetable genomic alterations that are correlated with the likelihood of response to specific agents, particularly for lung cancer (2-4). Similar studies are desperately needed to discover promising targets for agents that increase the radiotherapeutic ratio.

Herein below is reported a high-throughput platform that measures radiation survival and leverages cancer genomic data to provide genotype-specific therapies.

Therapeutic Regimens of the Invention

Compounds that are PI3 kinase inhibitors, such as NVP-BKM120, and other compounds that inhibit PI3 kinase activity, are useful as radiation sensitizing agents for the treatment of neoplasias, such as lung cancer. Preferably, PI3 kinase inhibitors, such as NVP-BKM120, and other compounds that inhibit PI3 kinase activity, are used in combination with radiation for the treatment of neoplasia.

A PI3K inhibitor, such as NVP-BKM120, may be administered prior to radiation therapy. In one embodiment, an effective amount of NVP-BKM120 is administered 1-24 hours, 1-3 days, or 3-7 days prior to radiation therapy. In another embodiment, a PI3K inhibitor, such as NVP-BKM120, is administered at about the same time as radiation therapy, i.e., concurrently or within 5-30 minutes of the time that radiation therapy commences. In yet another embodiment, In one embodiment, an effective amount of NVP-BKM120 is administered 1-24 hours, 1-3 days, or 3-7 days subsequent to radiation therapy.

Compounds of the Invention

Examples of compounds of the invention include PI3 kinase inhibitors, including agents that selectively inhibit PI3 kinase alpha (e.g., NVP-BKM120) and pharmaceutically acceptable salts thereof.

The structure of CAS 944396-07-0, 5-(2,6-dimorpholinopyrimidin-4-yl)-4-(trifluoromethyl)pyridin-2-amine:

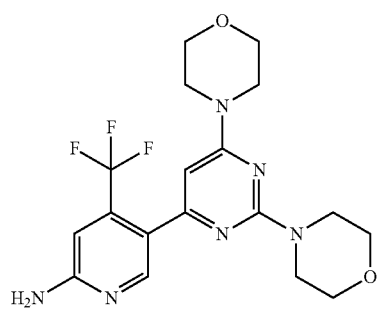 [SMILES: Nc1cc(C(F)(F)F)c(-c2cc(N3CCOCC3)nc(N3CCOCC3)n2)cn1]

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound disclosed herein, e.g., NVP-BKM120 having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

Screening Methods

As described above, the invention provides specific examples of chemical compounds that enhance the response of neoplastic cells to radiation. However, the invention is not so limited. The invention further provides a simple means for identifying agents (including nucleic acids, peptides, small molecule inhibitors, and mimetics) that are capable of acting as radiation sensitizers. Such compounds are also expected to be useful for the treatment or prevention of a neoplasia (e.g., lung cancer).

Virtually any agent that inhibits PI3 kinase activity, most preferably that acts as a may be employed in the methods of the invention. Methods of the invention are useful for the high-throughput low-cost screening of candidate agents that reduce, slow, or stabilize the growth or proliferation of a neoplasia. A candidate agent that reduces NRF2 activity is then isolated and tested for activity in an in vitro assay or in vivo assay for its ability to reduce neoplastic cell proliferation, increase the efficacy of radiation, and/or increase neoplastic cell death. One skilled in the art appreciates that the effects of a candidate agent on a cell is typically compared to a corresponding control cell not contacted with the candidate agent. Thus, the screening methods include comparing the proliferation of a neoplastic cell contacted by a candidate agent to the proliferation of an untreated control cell.

In one working example, one or more candidate agents are added at varying concentrations to the culture medium containing a neoplastic cell. PI3 kinase inhibitors and other radiation sensitizers are considered useful in the invention; such an agent may be used, for example, as a therapeutic to prevent, delay, ameliorate, stabilize, or treat a neoplasia. An agent identified according to a method of the invention is locally or systemically delivered to treat a neoplasia in situ.

If one embodiment, the effect of a candidate agent may, in the alternative, be measured at the level of NRF2 polypeptide production using the same general approach and standard immunological techniques, such as Western blotting or immunoprecipitation with an antibody specific for NRF2. For example, immunoassays may be used to detect or monitor the expression of NRF2 in a neoplastic cell. In one embodiment, the invention identifies a polyclonal or monoclonal antibody (produced as described herein) that is capable of reducing the expression or biological activity of a NRF2 polypeptide. A compound that reduces the expression or activity of a NRF2 polypeptide is considered particularly useful. Again, such an agent may be used, for example, as a therapeutic to prevent or treat a neoplasia.

Test Compounds and Extracts

In general, NRF2 antagonists (e.g., agents that specifically bind and reduce the activity of a NRF2 polypeptide) are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Agents used in screens may include known those known as therapeutics for the treatment of a neoplasia. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222: 301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have PI3 kinase inhibitory activity further fractionation of the positive lead extract is necessary to isolate molecular constituents responsible for the observed effect. Thus, the goal of the extraction, fractionation, and purification process is the careful characterization and identification of a chemical entity within the crude extract that reduces neoplastic cell proliferation or viability. Methods of fractionation and purification of such heterogenous extracts are known in the art. If desired, compounds shown to be useful as therapeutics are chemically modified according to methods known in the art.

Pharmaceutical Therapeutics

In other embodiments, agents discovered to have medicinal value using the methods described herein are useful as a drug or as information for structural modification of existing compounds, e.g., by rational drug design. Such methods are useful for screening agents having an effect on a neoplasia.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, although in certain instances lower amounts will be needed because of the increased specificity of the compound. A compound is administered at a dosage that is cytotoxic to a neoplastic cell, that reduces NRF2 expression or biological activity, or that reduces the proliferation, survival, or invasiveness of a neoplastic cell as determined by a method known to one skilled in the art, or using any that assay that measures the expression or the biological activity of a NRF2 polypeptide.

Formulation of Pharmaceutical Compositions

The administration of a compound for the treatment of a neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active anti-neoplasia therapeutic substance). The coating may be applied on the solid dosage form in a similar manner as that described in Encyclopedia of Pharmaceutical Technology, supra.

At least two anti-neoplasia therapeutics may be mixed together in the tablet, or may be partitioned. In one example, the first active anti-neoplasia therapeutic is contained on the inside of the tablet, and the second active anti-neoplasia therapeutic is on the outside, such that a substantial portion of the second anti-neoplasia therapeutic is released prior to the release of the first anti-neoplasia therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active anti-neoplasia therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

The present invention provides methods of treating neoplastic disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplastic disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplastic disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which NRF2 may be implicated.

Combination Therapies

An anti-neoplasia therapeutic, such as a PI3 kinase inhibitor, may be administered in combination with radiation.

Kits or Pharmaceutical Systems

The present compositions may be assembled into kits or pharmaceutical systems for use in ameliorating a neoplasia. Kits or pharmaceutical systems according to this aspect of the invention comprise a carrier means, such as a box, carton, tube or the like, having in close confinement therein one or more container means, such as vials, tubes, ampoules, bottles and the like. The kits or pharmaceutical systems of the invention may also comprise associated instructions for using the agents of the invention.

The present invention provides methods of treating neoplastic disease and/or disorders or symptoms thereof which comprise administering radiation in combination with a therapeutically effective amount of a pharmaceutical composition comprising a PI3 kinase inhibitor (e.g., to a subject (e.g., the selective PI3K inhibitor, NVP-BKM120) to a mammal such as a human. Thus, one embodiment is a method of treating a subject suffering from or susceptible to a neoplastic disease (e.g., lung cancer, non-small cell lung cancer) or a disorder or symptom thereof. The method includes the step of administering to the mammal a therapeutic amount of a compound herein sufficient to treat the neoplasia, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which radiation sensitization may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a neoplastic disorder or symptoms thereof associated with resistance to radiation therapy, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Development and Validation of a High-Throughput Radiation Survival Assay

To profile radiation response in lung SqCC cell lines, clonogenic assays were performed on 18 lines after exposure to 0, 2, 5, or 8 Gy of γ-rays. LOU-NH91 and SK-MES-1 were non-clonogenic and SW1573 had prohibitively low plating efficiencies. Therefore, the survival for 15 of the 18 available cell lines was analysed (FIG. 1 and Table 1).

TABLE 1

Clonogenic survival of lung SqCC after radiation

| Cell Line | SF2 | SF5 | SF8 |
|---|---|---|---|
| LK-2 | 0.75 | 0.34 | 0.05 |
| EBC-1 | 0.5 | 0.12 | 0.01 |
| SQ-1 | 0.43 | 0.12 | 0.01 |
| HARA | 0.69 | 0.37 | 0.11 |
| HCC15 | 0.7 | 0.29 | 0.05 |
| H2170 | 0.68 | 0.18 | 0.04 |
| H520 | 0.48 | 0.08 | 0.01 |
| HCC95 | 0.69 | 0.28 | 0.08 |
| H226 | 0.57 | 0.14 | 0.05 |
| SW900 | 0.68 | 0.14 | 0.04 |
| CALU-1 | 0.56 | 0.15 | 0.03 |
| LC-1/SQ-SF | 0.66 | 0.12 | 0.02 |
| LUDLU-1 | 0.76 | 0.29 | 0.09 |
| RERF-LC-AI | 0.51 | 0.1 | 0.01 |
| KNS-62 | 0.6 | 0.35 | 0.11 |

Radiation response in the same 18 cell lines was measured in a format amenable to high-throughput profiling. Growth measurements in 384-well plates were first optimized. The linear range for proliferation as a function of cell density was determined for each cell line; representative plots and light microscopy images for LUDLU-1 and EBC-1 after incubation for 9 days are shown in FIGS. 2A and 2C. Using cell densities in the linear range of plating, growth (0 Gy) and recovery of growth after exposure to a range of doses of radiation was assessed by plotting relative luminescence units (RLU) as a function of time (FIG. 2B).

Figure 2:
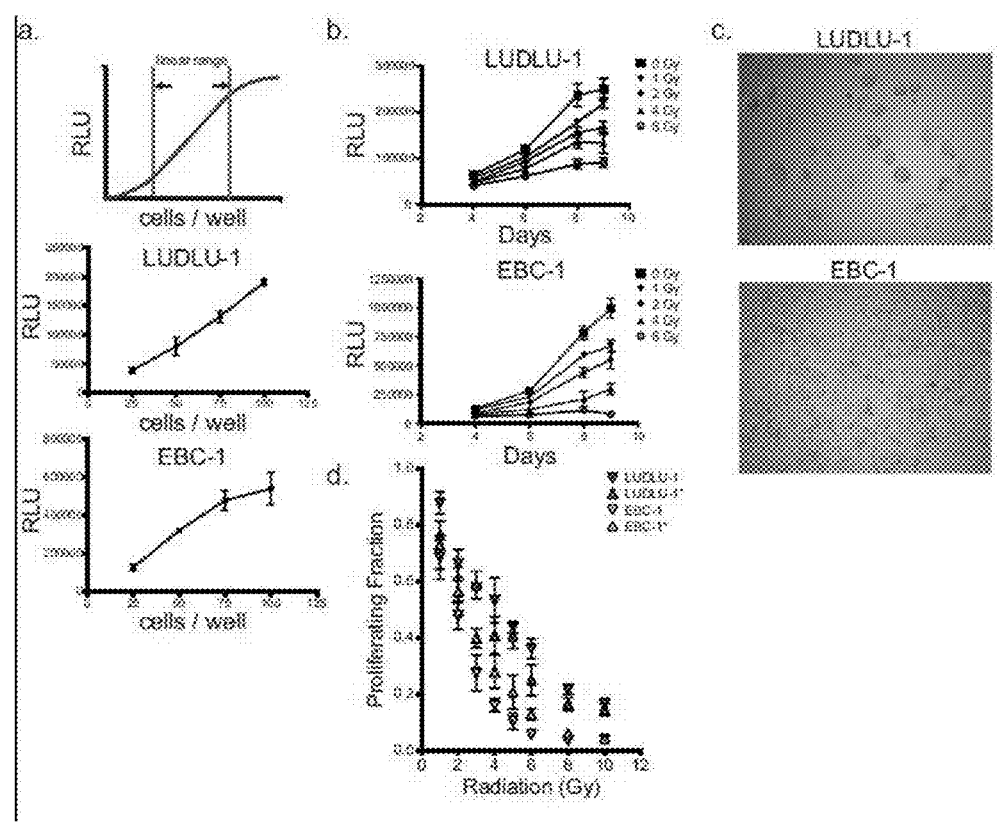
FIG. 2 shows results of a high-throughput profiling of survival following exposure to γ-radiation. Cells were plated at cell densities ranging from 25-300 cells in 70 μL of media per well. Luminescence-based detection of cellular ATP, a surrogate measure of cell number was performed.

The proliferating fraction (mean RLU at dose x/mean RLU of control) was plotted as a function of dose at 9 days for all cell lines (FIG. 2D and Table 2).

TABLE 2

High-throughput profiling of lung SqCC after radiation

|  | HARA | EBC-1 | H2170 | HCC15 | H226 | HCC95 | LK-2 | SW900 | KNS-62 | RERF-LC-AI |
|---|---|---|---|---|---|---|---|---|---|---|
| PF1 | 0.75 | 0.71 | 0.68 | 0.71 | 0.76 | 0.78 | 0.87 | 0.72 | 0.82 | 0.58 |
| PF2 | 0.79 | 0.53 | 0.6 | 0.6 | 0.44 | 0.64 | 0.9 | 0.62 | 0.67 | 0.42 |
| PF3 | 0.68 | 0.34 | 0.35 | 0.52 | 0.31 | 0.45 | 0.7 | 0.4 | 0.59 | 0.32 |
| PF4 | 0.52 | 0.23 | 0.28 | 0.33 | 0.2 | 0.36 | 0.42 | 0.29 | 0.45 | 0.16 |
| PF5 | 0.4 | 0.16 | 0.2 | 0.23 | 0.14 | 0.27 | 0.33 | 0.15 | 0.43 | 0.12 |

TABLE 2-continued

High-throughput profiling of lung SqCC after radiation

| | | | | | | | | | | |
|---|---|---|---|---|---|---|---|---|---|---|
| PF6 | 0.27 | 0.1 | 0.14 | 0.2 | 0.07 | 0.18 | 0.19 | 0.11 | 0.28 | 0.07 |
| PF8 | 0.12 | 0.05 | 0.05 | 0.13 | 0.02 | 0.09 | 0.06 | 0.06 | 0.17 | 0.02 |
| PF10 | 0.05 | 0.05 | 0.03 | 0.1 | 0.01 | 0.04 | 0.01 | 0.04 | 0.08 | 0.01 |

| | LOU-NH91 | SW1573 | SK-MES-1 | SQ-1 | LC-1/SQ-SF | LUDLU-1 | H520 | CALU-1 |
|---|---|---|---|---|---|---|---|---|
| PF1 | 0.95 | 0.85 | 0.78 | 0.68 | 0.78 | 0.83 | 0.66 | 0.74 |
| PF2 | 0.68 | 0.71 | 0.63 | 0.53 | 0.57 | 0.62 | 0.4 | 0.61 |
| PF3 | 0.48 | 0.61 | 0.46 | 0.32 | 0.41 | 0.59 | 0.27 | 0.48 |
| PF4 | 0.41 | 0.56 | 0.41 | 0.25 | 0.3 | 0.48 | 0.21 | 0.37 |
| PF5 | 0.32 | 0.42 | 0.29 | 0.16 | 0.24 | 0.43 | 0.15 | 0.30 |
| PF6 | 0.15 | 0.39 | 0.2 | 0.1 | 0.12 | 0.31 | 0.11 | 0.22 |
| PF8 | 0.12 | 0.33 | 0.08 | 0.06 | 0.04 | 0.2 | 0.05 | 0.14 |
| PF10 | 0.07 | 0.33 | 0.03 | 0.05 | 0.03 | 0.16 | 0.04 | 0.09 |

Figure 3:
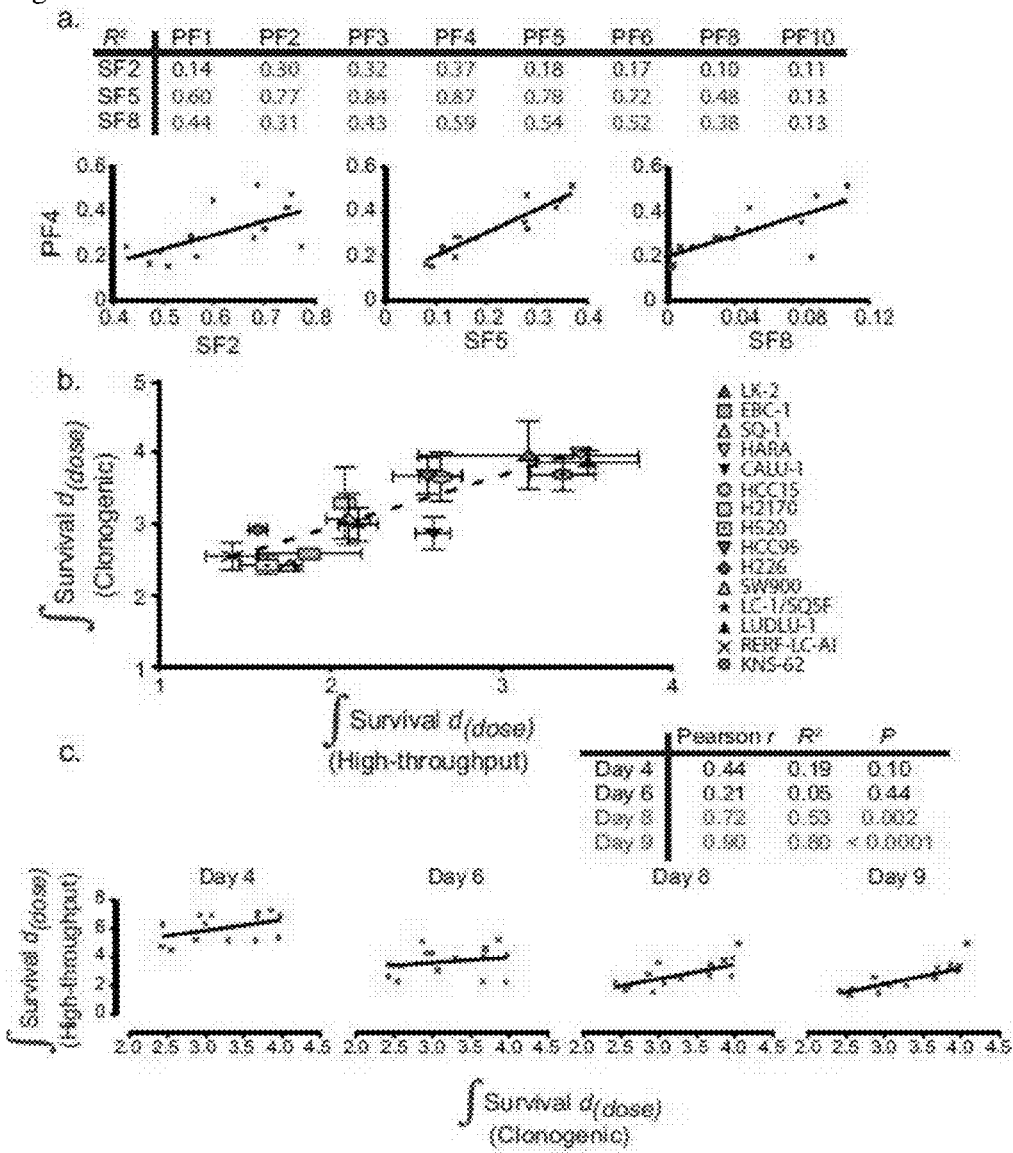
FIG. 3 shows that the high-throughput platform accurately profiles lung squamous cancer cell lines.

Next examined was whether the high-throughput platform correlated with clonogenic survival following exposure to radiation. The extent of correlation between individual doses (for each cell line, n≥2) was assessed. $R^2$ values were calculated using the average value for each cell line by comparing surviving fraction at dose x (SFx) with proliferating fraction at dose x (PFx), generating a correlation table across the different doses of radiation (FIG. 3A). These data indicate that high-throughput proliferation better approximates clonogenic assay measurements at doses greater than 2 Gy. Among the PFx doses, $R^2$ values were highest for PF4. Therefore, the dose which best approximates clonogenic survival is within the $GI_{50}$ range for all cell lines (3-5 Gy).

For each proliferation and clonogenic experiment performed, survival was integrated as a function of dose and values were generated for each cell line. Mean integral survival for 15 cell lines (for each cell line, n≥2) was calculated and compared to values from the clonogenic assay (FIG. 3B). Proliferation and colony integral survival values were significantly correlated, with Pearson r=0.90, $R^2$=0.80, and P<0.0001. Linear regression showed a slope of 0.73±0.1.

Correlation between clonogenic survival and the high-throughput platform was next assessed as a function of time (FIG. 3C). The concordance between clonogenic survival and proliferation after radiation exposure is time dependent, reaching statistical significance on day 8 and achieving the highest correlation on day 9 (FIG. 3C).

Figure 4:
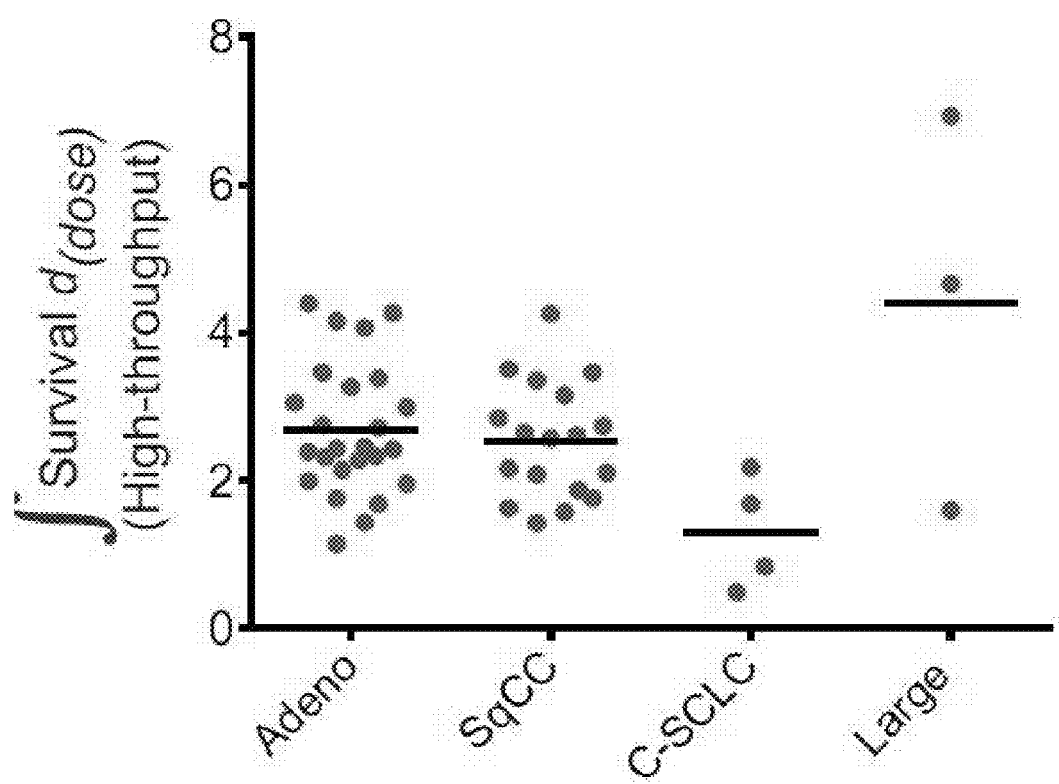
FIG. 4 shows results of high-throughput profiling of lung cancer cell lines. Integral survival was calculated from high-throughput platform profiling of the indicated cell lines, all derived from the lung. A scatter plot stratified by histology is displayed. For SqCC, n≥2, for all other cell lines, n=1. Solid bars represent the mean in each category. Classical small cell lung carcinoma (C-SCLC) lines were most sensitive, large cell lung carcinoma cell lines least sensitive, and lung adenocarcinoma cell lines showed intermediate sensitivity. These in vitro results minor clinical observations suggesting that lung adenocarcinoma, C-SCLC, and large cell carcinoma generally have radiation response similar to, more sensitive than, and more resistant than lung SqCC, respectively. There is a greater than 7-fold difference in integral survival between the most sensitive and resistant cell line indicating that the platform can resolve a broad range of survival after radiation.

In addition to squamous cell lung carcinoma cell lines, a broader diversity of lung cancer cell lines were assayed for radiation response. It was found that the results of the high-throughput platform shown here are broadly consistent with the literature across multiple lung cancer cell types (21, 22) (FIG. 4). Taken together, these results indicate that the high-throughput platform facilitated the profiling of cell lines for radiation response and, despite some differences between the two assays, closely approximated clonogenic survival by most radiation response parameters.

Example 2

NFE2L2 Activation Regulates Radiation Resistance in Lung SqCC

NFE2L2 and KEAP1 are key regulators of oxidative and electrophilic stress response (23, 24). Exposure to reactive oxygen species (ROS) directly modifies cysteine residues in KEAP1, leading to NRF2 stabilization and translocation into the nucleus. NRF2 is responsible for the activation of cytoprotective genes, including genes that scavenge ROS (25, 26). Indeed, NRF2 activity has been demonstrated to confer both radiation resistance and lower endogenous levels of ROS (27, 28).

Figure 5:
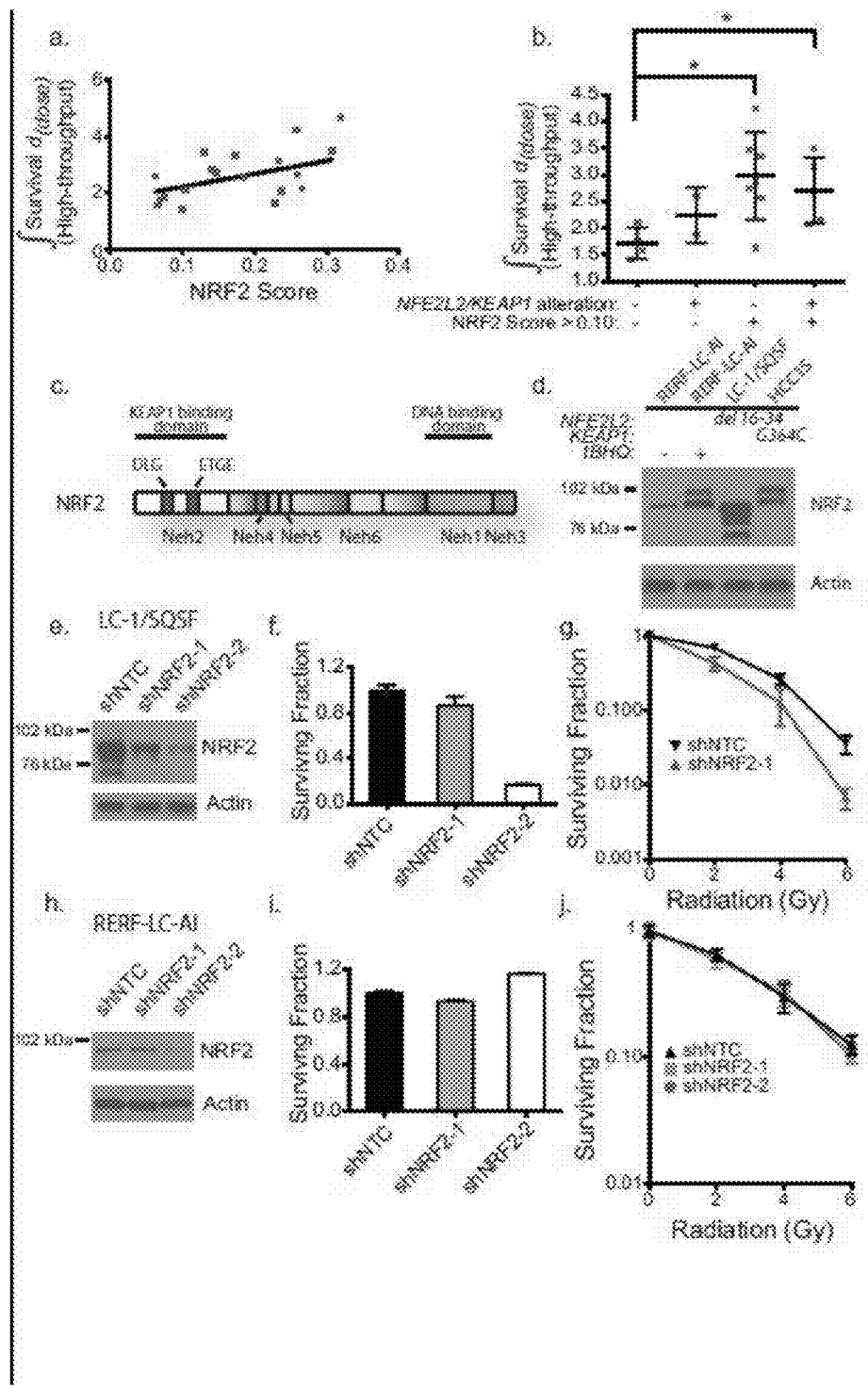
FIG. 5 shows that NFE2L2 activation regulates radiation resistance and is a target for radiotherapeutic sensitization.

The extent to which NRF2 mediates therapeutic resistance has yet to be fully assessed across a large panel of cell lines or in lung SqCC. To assess NRF2's role as a regulator of radiation resistance in lung SqCC cell lines, a summary gene signature score for NRF2 activation was calculated (see Methods) for each cell line profiled and determined the extent of correlation with radiation response. Survival after radiation exposure was significantly correlated with NRF2 score, with Pearson r=0.47, $R^2$=0.22, and P=0.047 (FIG. 5A). Directed sequencing of NFE2L2 and KEAP1 revealed a high frequency of alterations in lung SqCC cell lines (Table 3).

TABLE 3

Mutations in NFE2L2 and KEAP1 in lung SqCC cell lines.

| Cell Line | EBC-1 | CALU-1 | LK-2 | HCC-15 | LC-1F/SQSF | LUDLU-1 | H2170 |
|---|---|---|---|---|---|---|---|
| NFE2L2 | D77V | P128L | E79K | | del 16-34 | | |
| KEAP1 | | | | G364C | | E258* | R336* |

*non-sense mutation; del, deletion

Radiation response was stratified by mutation and high NRF2 score, defined as a value greater than the median (0.10) (FIG. 5B). These data demonstrated that high NRF2 score is a good predictor of radiation resistance.

Disruption of the KEAP1 binding sites within NRF2 ($L_{23}$WRQDIDLG and $D_{77}$EETGE) (FIG. 5C) have been previously shown to decrease NRF2-KEAP1 binding, inhibit KEAP1-mediated degradation, and ultimately promote transcriptional activity of NRF2 (29). Consistent with these results, both NFE2L2 mutant LC-1/SQSF (NRF2 score, 0.27) and KEAP1 mutant HCC15 (NRF2 score, 0.26) cell lines showed greater NRF2 protein levels compared to NFE2L2/KEAP1 wild type cell line RERF-LC-AI (NRF2 score, 0.10) (FIG. 5D). The magnitude of NRF2 stabilization in LC-1/SQSF and HCC15 approximated that observed for RERF-LC-AI cells treated with tert-Butylhydroquinone (tBHQ), a chemical promoter of NRF2 stabilization and transcriptional activity (30).

To determine the role of NRF2 in regulating radiation response, LC-1/SQSF cells that stably express shRNAs against NRF2 were established. Two lentiviral-inducible NRF2-targeted shRNAs (shNRF2-1 and shNRF2-2) significantly reduced the expression of endogenous mutant NRF2 compared with control shNTC (FIG. 5E). Clonogenic survival was tested after lentiviral-induction in cells that stably expressed shNTC, shNRF2-1, and shNRF2-2. Cells that stably expressed shNRF2-2 had significantly diminished clonogenic capacity, correlating with the extent of reduced NRF2 protein, and therefore could not be evaluated for radiation response (FIG. 5F). To determine whether NRF2 has a role in resistance to radiation, shNTC and shNRF2-1 infected LC-1/SQSF cells were treated with radiation and then their clonogenic survival was examined. NRF2-down-regulated cells were more sensitive to radiation than control cells (FIG. 5G). It is important to note that this experiment models single fraction treatment. Patients generally receive multiple fractions of treatment, with a predicted compounding of the sensitization effect.

To determine whether NRF2 has a role in radiation resistance in a cell line that does not contain activating mutations in NFE2L2 or KEAP1, RERF-LC-AI cells were established that stably express shRNAs against NRF2. shNRF2-1 had a minimal affect on NRF2 protein level while shNRF2-2 significantly reduced the expression of endogenous NRF2 compared with control shNTC (FIG. 5H). In contrast to the diminished clonogenic capacity and radiosensitivity phenotype observed in LC-1/SQSF, significant reduction of NRF2 in RERF-LC-AI did not result in any observable decrease in clonogenic capacity or radiation sensitivity (FIGS. 5I and 5J). Taken together, these data indicate that mutation and activation of the NFE2L2 pathway confers radiation resistance in lung SqCC.

Figure 6:
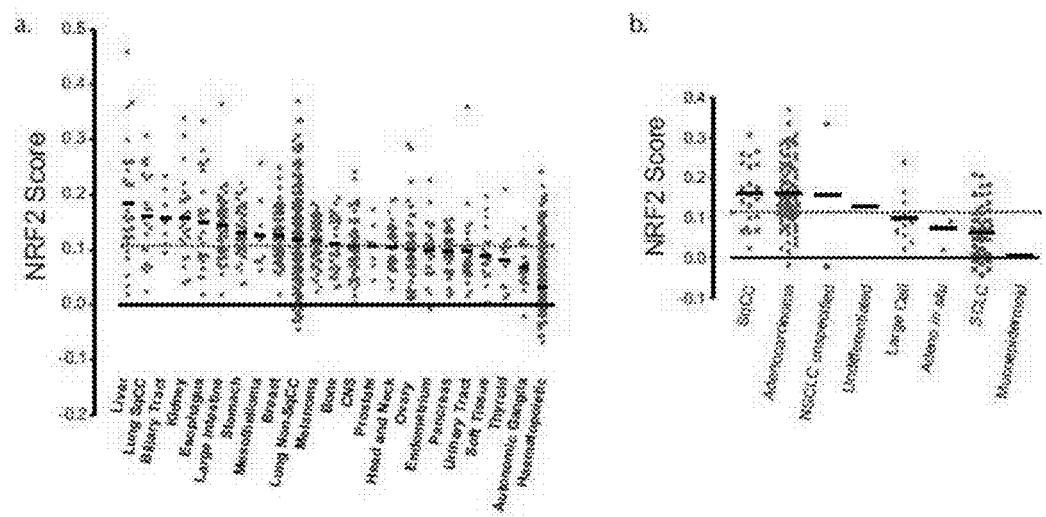
FIG. 6, Panels (a) and (b) show that NFE2L2 is frequently activated in human cancers.

To determine the extent of activation of NFE2L2 across multiple tumor types, a summary gene signature score for NRF2 activation was calculated for each cell line in the CCLE (967 cell lines) (FIGS. 6A and 6B). This indicates that activation of NRF2 is not unique to specific tumor lineages and nominates it as radiotherapeutic target in a wide range of malignancies.

Example 3

PI3K Inhibitors are NRF2 Antagonists and Radiation Sensitizers

Figure 7:
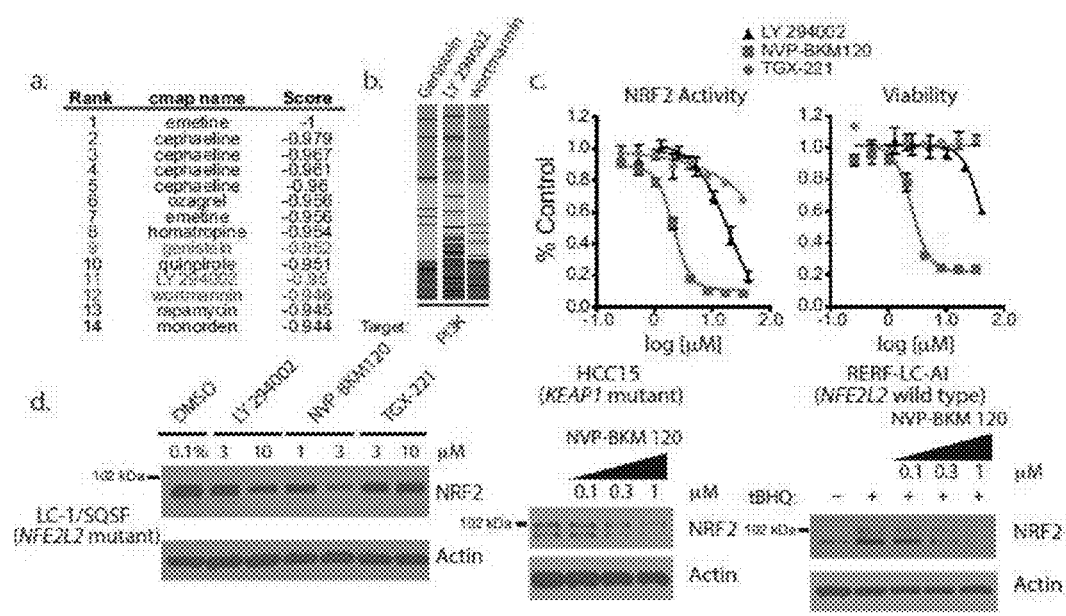
FIG. 7 shows that inhibition of PI3K antagonizes NRF2.

Multiple in silico approaches of high-throughput discovery have emerged, including the Connectivity Map (cmap), a Web-based tool that comprises a large gene expression database generated from human cancer cell lines treated with different chemicals (31, 32). Several studies have demonstrated the utility of chemical genomics in modulating biological processes by querying gene expression patterns (33-38). A screened for compounds whose expression negatively correlates with the NFE2L2 signature was carried out. The results of the screen are listed by rank order using a matching algorithm based on the non-parametric rank-ordered Kolmogorov-Smirnov statistics transformed to a 'connectivity score' ranging from +1 to −1 (FIG. 7A). A negative score denotes a negative correlation between a query signature and an individual chemical, indicating that the PI3K inhibitors genistein, LY 294002, and wortmannin are putative NRF2 antagonists (see FIG. 7B for a "bar view" of individual cmap instances).

Expression of active PI3K has long been implicated in regulating therapeutic (chemical and radiation) resistance (39, 40), although the precise mechanism(s) of resistance remain poorly defined. NRF2 has previously been show to require cooperation from active PI3K-Akt signaling (41). These results, coupled with the in silico findings above, suggested that PI3K-Akt inhibition may be an effective strategy to antagonize NRF2 and by extension effect radiosensitization. To test this, LC-1/SQSF cells were generated that stably express hNQO1-ARE-luc, containing cis-acting antioxidant response regulatory elements in the 5'-flanking region of NAD(P)H:quinone oxidoreductase (NQO1) (19), a gene induced by NRF2. Luciferase activity was measured in LC-1/SQSF, hNQO1-ARE-luc cells after incubation with LY 294002, NVP-BKM120, or TGX-221. The pan-PI3K inhibitors LY 294002 and NVP-BKM120, but not the PI3Kβ selective inhibitor TGX-221, resulted in a significant decrement in NRF2 activity (top panel, FIG. 7C). Cellular viability was measured after incubation with LY 294002, NVP-BKM120, or TGX-221. The decrement in cellular viability at 48 hours (lower panel, FIG. 7C) mirrored the effect on NRF2 activity at 24 hours. This correlation between viability and NRF2 activity suggests that either LC-1/SQSF cells are dependent on NRF2 for viability (suggested by FIG. 2F) or that toxicity leads to a non-specific decrement in NRF2 activity.

To address this, NRF2 protein level were measured in the same cells after incubation with LY 294002, NVP-BKM120, or TGX-221 at 24 hours, an interval of time that showed a negligible decrement in viability (viability >90%). Consistent with the reporter assay, LY 294002 and NVP-BKM120, but not TGX-221, resulted in a significant decrement in NRF2 protein level (FIG. 7D). NVP-BKM120 resulted in a similar decrement in NRF2 protein level for HCC15 and RERF-LC-AI cells treated with tBHQ. These results indicate that an active PI3K pathway is required for NRF2 stability and that the putative target for NRF2 antagonism is PI3K through isoforms other than PI3Kβ.

Figure 8:
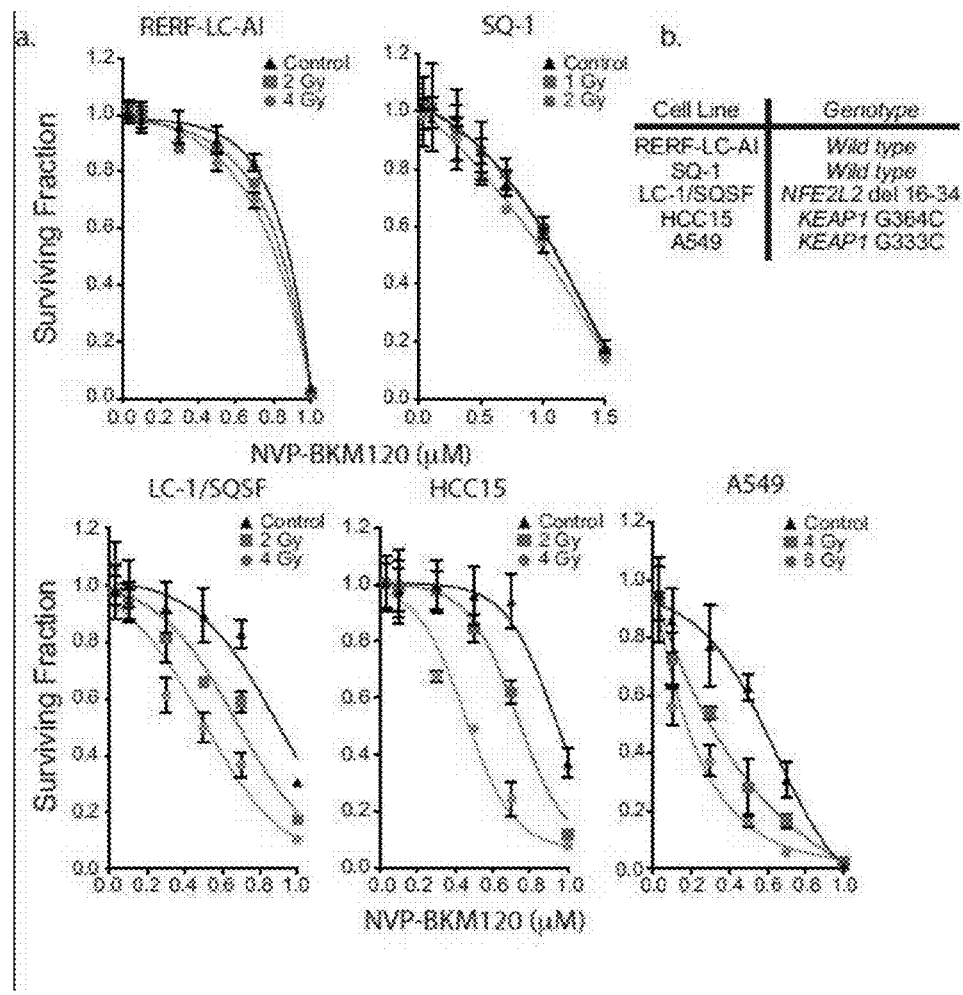
FIG. 8, Panels (a) and (b) show that inhibition of PI3K effects radiosensitization in cell lines with a NFE2L2 pathway alteration.

Since NRF2 down-regulation effects radiosensitization in LC-1/SQSF cells (FIG. 5), and NVP-BKM120 results in NRF2 down-regulation, NVP-BKM120 was predicted to function as a radiation sensitizer in cell lines with an active NRF2 pathway. LC-1/SQSF, HCC15, and A549 cells exposed to NVP-BKM120 and radiation showed a synergistic decrement in clonogenic survival compared to control (0 Gy) cells (FIG. 8). RERF-LC-AI and SQ-1 (NFE2L2 and KEAP1 wild type) cells showed significantly less synergy between NVP-BKM120 and radiation. These results indicate that treatments that antagonize NRF2-mediated transcription can be potent radiation sensitizers and suggest that the synergy between PI3K inhibitors and radiation are greater in cell lines with an active NRF2 pathway.

Example 4

Figure 9:
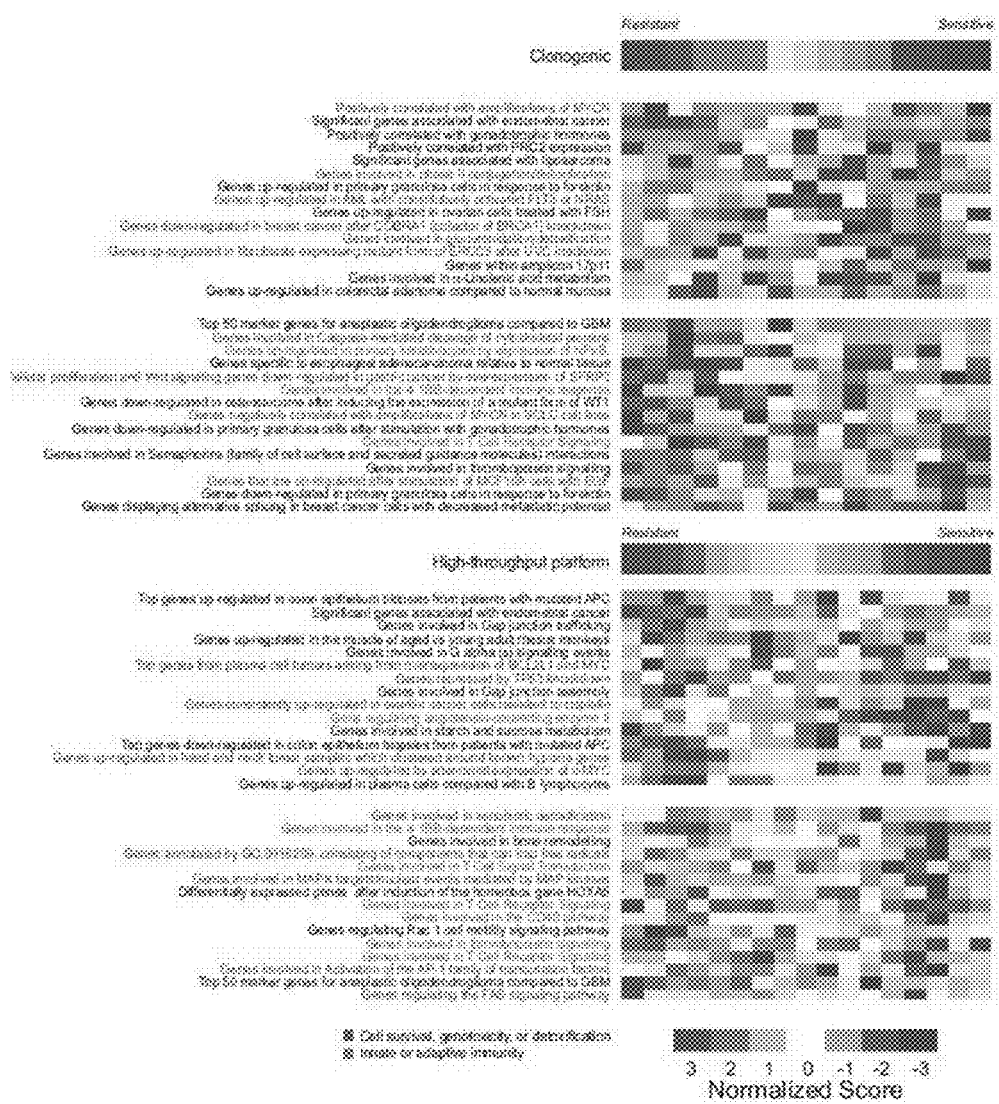
FIG. 9 shows that ssGSEA identifies gene sets that correlate with radiation resistance (left) and sensitivity (right). Heat map of ssGSEA scores (red=positive, blue=negative). Top 15 gene sets are listed.
Figure 10:
FIG. 10 shows that ssGSEA identifies gene sets that correlate with radiation resistance (left) and sensitivity (right). Heat map of ssGSEA scores (red=positive, blue=negative). Top 50 gene sets are listed.

Gene Expression Analysis Identifies Pathways that Correlate with Radiation Response in Lung SqCC Susceptibility of tumors to radiation is regulated by several pathways mediating the cellular response to radiation-induced damage. To identify pathways that are differentially correlated with radiation response, ssGSEA projection was used (42) as a hypothesis-generating gene set identification tool.

ssGSEA identifies biologically relevant gene sets that correlate with a functional output by estimating the degree to which an established gene set is overrepresented at the (top or bottom) of the sorted gene expression values list in each sample. To achieve this, an ssGSEA enrichment score was calculated, which is based on the weighted difference of the Empirical Cumulative Distribution Functions of the genes in the set relative to the genes not included in an individual set (42). The result is a single score per cell line per gene set, transforming the original dataset into a more interpretable higher-level description. Gene sets were obtained from the C2 sub-collection of the Molecular Signatures database (MSigDB) (43), an additional collection of oncogenic signatures, and other cancer-related gene sets curated from the literature, resulting in a dataset that has 4,628 pathway profiles for each sample. The association between the ssGSEA profiles for each gene set and the radiation response profile is then determined using an information-based similarity metric (RNMI) (see Methods) and the dataset is resorted based on this metric to identify correlates and anti-correlates with radiation survival (FIGS. 9 and 10).

The profiles of each gene set/pathway was compared with the radiation response scores (integral survival by clonogenic assay and high-throughput platform). The ssGSEA scores are displayed in a heatmap with the top 15 gene sets that correlate and anti-correlate with radiation survival (FIG. 9 and Table 3). Analysis of the both the top 15 and top 50 gene sets (FIGS. 9 and 10) revealed overlap in the gene sets identified by the clonogenic assay and high-throughput platform. Moreover, we inserted the calculated ssGSEA enrichment scores utilizing the NRF2 gene set and identified NRF2 activation as positively correlated with radiation resistance; the NRF2 gene set was ranked number 48 using survival data from the high-throughput platform. These results indicate that ssGSEA is a robust gene set identification tool.

An analysis of the gene sets that differentially correlated with radiation survival suggested that pathways implicated in cell survival, genotoxicity, detoxification and innate or adaptive immunity can regulate radiation response. Moreover, the identity of individual gene sets and their correlation with radiation response can identify and aid in the validation of targets for potential radiotherapeutic sensitization. For example, a TP53 gene set was identified by ssGSEA (rank number seven in the high-throughput platform analysis (FIGS. 9 and 10), suggesting that TP53 transcriptional activation mediates radiation resistance. Despite a well defined role for TP53 in regulation of DNA repair, cell cycle arrest, and apoptosis after genotoxic stress (44), the predictive role of TP53 mutations in radiation response has been uncertain.

Beyond demonstrating a proof of the concept that ssGSEA can identify know regulators of radiation response, the role of alterations in TP53 on radiation response across a panel of cell lines was examined. TP53 mutations, LOH, and mRNA levels were assessed in the lung SqCC cell lines profiled for radiation response (Table 4).

TABLE 4

| MSigDB Gene Sets |
|---|
| Clonogenic Assay |
| Correlates |
| KIM_MYCN_AMPLIFICATION_TARGETS |
| WONG_ENDOMETRIUM_CANCER_UP |
| SASSON_RESPONSE_TO_FORSKOLIN |
| PRC2_SUZ12_UP.v1.UP |
| NIELSEN_LIPOSARCOMA_UP |
| REACTOME_PHASE_II_CONJUGATION |
| SASSON_RESPONSE_TO_GONADOTROPHINS |
| NEBEN_AML_WITH_FLT3_OR_NRAS |
| JI_RESPONSE_TO_FSH |
| AIYAR_COBRA1_TARGETS_DN |
| REACTOME_GLUCURONIDATION |
| DIACOSTA_LOW_DOSE_UV_RESPONSE_VIA_ERCC3_XPCS |
| NIKOLSKY_BREAST_CANCER_17P11_AMPLICON |
| KEGG_ALPHA_LINOLENIC_ACID_METABOLISM |
| SABATES_COLORECTAL_ADENOMA_UP |
| Anti-correlates |
| NUTT_GBM_VS_AO_GLIOMA_UP |
| REACTOME_CASPASE_MEDIATED_CLEAVAGE_OF_CYTOSKELETAL_PROTEINS |
| HNATAT_NFKB_TARGETS_KERATINOCYTE |
| WANG_ESOPHAGUS_CANCER_VS_NORMAL |
| BIOCARTA_41BB_PATHWAY |
| NOJIMA_SFRP2_TARGETS |
| KIM_WT1_TARGETS_8HR |
| KIM_MYCN_AMPLIFICATION_TARGETS_DN |
| SASSON_RESPONSE_TO_GONADOTROPHINS_DN |
| BIOCARTA_TCR_PATHWAY |
| REACTOME_SEMAPHORIN_INTERACTIONS |
| BIOCARTA_TPO_PATHWAY |
| AMIT_EGF_RESPONSE_40_MCF10A |
| SASSON_RESPONSE_TO_FORSKOLIN_DN |
| LEE_METASTASIS_AND_ALTERNATIVE_SPLICING |
| High-throughput Platform |
| Correlates |
| MILICIC_FAMILIAL_ADENOMATOUS_POLYPOSLS_UP |
| WONG_ENDOMETRIUM_CANCER_UP |
| REACTOME_GAP_JUNCTION_TRAFFICKING |

TABLE 4-continued

MSigDB Gene Sets

Figure 11:
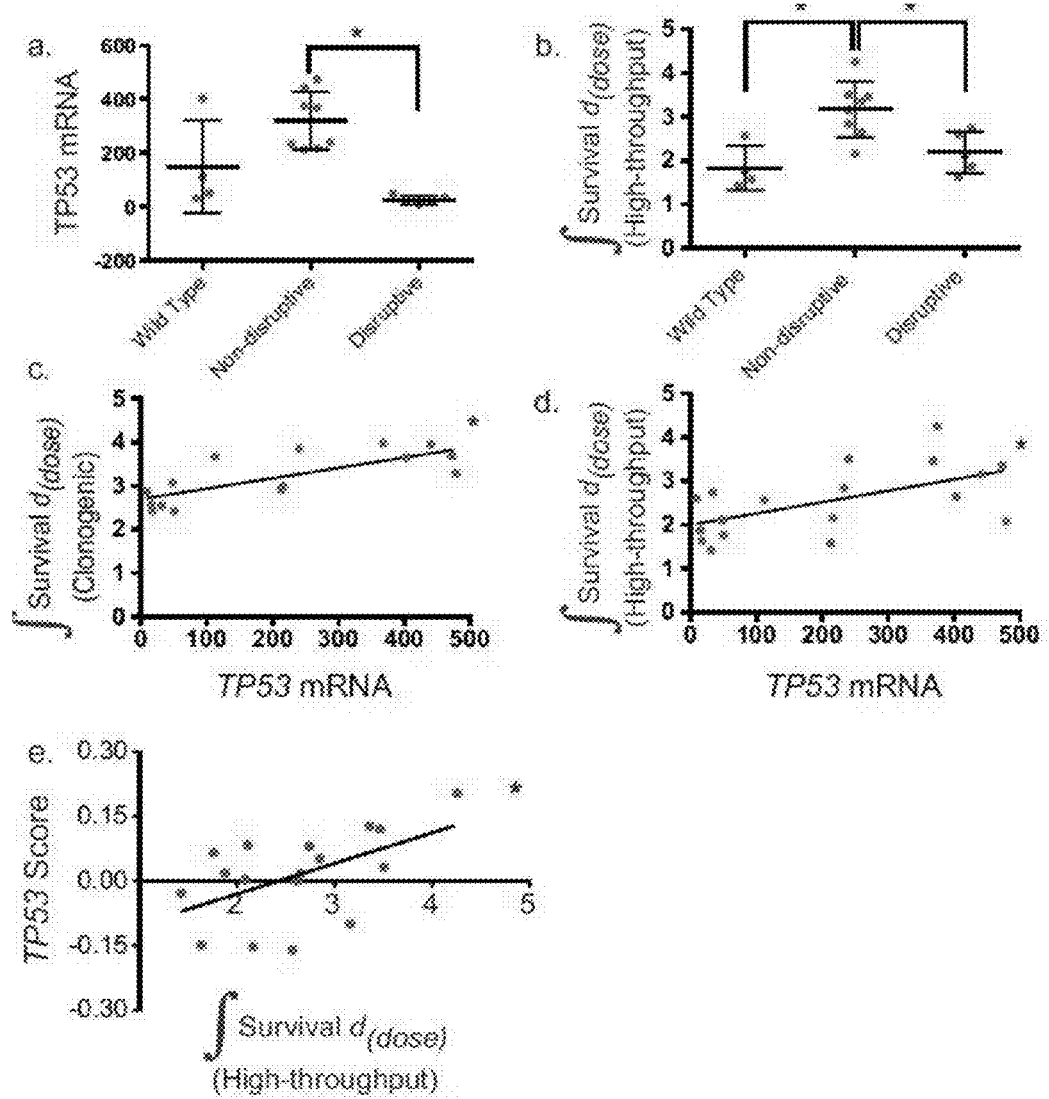
FIG. 11 shows that TP53 is frequently altered in lung SqCC lines and its activation correlates with radiation resistance.

KAYO_AGING_MUSCLE
REACTOME_G_ALPHA_S_SIGNALLING_EVENTS
BOYLAN_MULTIPLE_MYELOMA_PCA3
P53_DN.v2_DN
REACTOME_GAP_JUNCION_ASSEMBLY
LI_CISPLATIN_RESISTANCE_UP
BIOCARTA_ACE2_PATHWAY
KEGG_STARCH_AND_SUCROSE_METABOLISM
MILICIC_FAMILIAL_ADENOMATOUS_POLYPOSIS_DN
WINTER_HYPOXIA_UP
MENSSEN_MYC_TARGETS
TARTE_PLASMA_CELL_VS_B_LYMPHOCYTE_UP
Anti-correlates REACTOME_XENOBIOTICS
BIOCARTA_41BB_PATHWAY
BIOCARTA_RANKL_PATHWAY
ANTIOXIDANT_ACTIVITY
ST_T_CELL_SIGNAL_TRANSDUCTION
REACTOME_MAPK_TARGETS_NUCLEAR_EVENTS_MEDIATED_BY_MAP_KINASES
CHEN_HOXA5_TARGETS_9HR_UP
BIOCARTA_TCR_PATHWAY
BIOCASTA_CD40_PATHWAY
BIOCARTA_RAC1_PATHWAY
BIOCARTA_TPO_PATHWAY
KEGG_T_CELL_RECEPTOR_SIGNALING_PATHWAY
REACTOME_ACTIVATION_OF_THE_AP1_FAMILY_OF_TRANSCRIPTION_FACTORS
NUTT_GBM_VS_AO_GLIOMA_UP
BIOCARTA_FAS_PATHWAY TP53 is frequently altered in the lung SqCC cell lines; eight of eighteen cell lines having missense mutations, all of which cluster in the DNA binding domain (aa. 101-305). TP53 mRNA levels were compared as a function of genotype and a significant difference in mRNA levels was found in cell lines with non-disruptive (missense mutation and intronic insertion) versus disruptive (non-sense mutation and deletion) alterations (P<0.0001) (FIG. 11A). Radiation response was compared as a function of genotype (FIG. 11B); there was a statistically significant difference between cell lines with wild type and non-disruptive mutations (P=0.004) and between cell lines with disruptive and non-disruptive mutations (P=0.01) in TP53. Integral survival values derived from clonogenic (FIG. 11C) and high-throughput platform (FIG. 11D) were plotted as a function of TP53 mRNA level and determined statistically significant correlations, $R^2$=0.57 and 0.33, P=0.001 and 0.01, respectively. A score for TP53 activation was computed using a previously described gene signature independent of the gene set included in ssGSEA (see Methods) and compared TP53 signature scores with radiation response.

High-throughput platform integral survival and TP53 score were significantly correlated, $R^2$=0.28, and P=0.03 indicating that a high TP53 signature score is a reasonable predictor of radiation response (FIG. 11E). Taken together, these data indicate that mutation and activation of the TP53 pathway is a significant predictor of radiation resistance in lung SqCC and highlights the utility of ssGSEA as a radiogenomic tool.

The clonogenic assay has long been considered the most reliable in vitro assay for measuring cell survival after exposure to radiation (45, 46). The clonogenic assay was adapted to measure radiation response in high-throughput form. Clonogenic growth was reconstituted by automated plating coupled with assay miniaturization into a 384-well per plate format. The platform accurately measured radiation survival in lung SqCC, closely approximating most radiation parameters obtained from clonogenic survival assays. It also appears to accurately profile lung cell lines from non-squamous lineages, suggesting that it can be applied broadly. It is not clear that measurement of proliferation at 9 days will be sufficient for the accurate profiling

TABLE 5

TP53 alterations, LOH, and mRNA levels in lung SqCC cell lines.

| Cell Line | HCC95 | H226 | SQ-1 | RERF-LC-AI | CALU-1 | H520 | EBC-1 | SW900 | SK-MES-1 | HARA |
|---|---|---|---|---|---|---|---|---|---|---|
| Genotype | WT | WT | WT | WT | del | W146* | E171* | Q167* | E298* | V143A |
| LOH | + | − | + | + | + | + | + | + | + | + |
| mRNA | 112 | 403 | 59 | 31 | 9 | 17 | 15 | 48 | 34 | 368 |

| Cell Line | HCC-15 | KNS-62 | LC-1F/SQSF | LK-2 | LOU-NH91 | LUDLU-1 | H2170 | SW1573 |
|---|---|---|---|---|---|---|---|---|
| Genotype | D259V | R249S | M237I | V272M | V143M | R248W | R158G | Intron (ins) |
| LOH | + | + | + | + | + | + | + | − |
| mRNA | 213 | 473 | 216 | 441 | 233 | 240 | 479 | 374 |

*non-sense mutation; del, deletion; ins, insertion; LOH, loss of heterozygosity of all cell lines, especially those at the extreme ends of growth rates. Nonetheless, minor adaptations of the platform (ie plating density and/or time to readout) should allow for the accurate profiling of a wide range of cell lines.

Compared to lung adenocarcinoma, there have been very few therapeutic advances in lung SqCC (47). Recently, greater insight into the genomic landscape of lung SqCC has been achieved (20), suggesting marked genomic complexity with frequent alterations in TP53, CDKN2A/RB1, NFE2L2/KEAP1/CUL3, and PI3K/AKT. To leverage cancer genomic data to advance knowledge of radiation tumor biology and therapeutic possibilities, we profiled the majority of lung squamous cell lines available for study. This work demonstrated that NFE2L2 mutations leading to pathway activation conferred radiation resistance. NFE2L2 pathway alterations are frequent occurrences in lung SqCC, found in 38% of the cell lines analyzed and 34% of TCGA samples (20). In a demonstration of the potential of combining the profiling of cell lines for radiation survival with expression-based databases, an in silico screen identified PI3K inhibitors as NRF2 antagonists and radiation sensitizers. Taken together, it is likely that these compounds will be therapeutic in genotype selected populations.

Single-sample gene set enrichment analysis (ssGSEA) was used as a hypothesis-generating computational approach to search for genetic markers and cellular pathways that correlate with radiation response. This approach identified several pathways previously implicated in radiation response including pathways mediating cell survival, genotoxicity, detoxification and innate or adaptive immunity. In a demonstration of the utility of ssGSEA, the role of TP53 mutation in regulating radiation response in lung SqCCs was analysed. This showed that TP53 missense mutation and pathway activation correlated with radiation resistance whereas TP53 disruptive mutations correlated with radiation sensitivity, a previously unappreciated distinction in lung SqCC. Moreover, these data are consistent with clinical outcomes. In patients with locally advanced NSCLC treated with radiation therapy alone, mutant TP53 (by directed sequencing of the DNA binding domain of the gene) resulted in a decreased treatment response (48-50).

In summary, the invention provides a high-throughput platform that accurately measures radiation survival in vitro and significantly facilitates the study of tumor radiogenomics. This approach incorporated ssGSEA and cmap for in silico high-throughput gene pathway and drug discovery. Together, these approaches outline a systematic and comprehensive strategy to identify key genetic correlates of radiation response and potent radiation modifiers whose effect is greatest in patients with specific genomic alterations.

The results described herein above were obtained using the following methods and materials.

Cell Culture and Irradiation.

Lung SqCC cell lines from the Cancer Cell Line Encyclopedia (CCLE) were authenticated per CCLE protocol (14) and grown in recommended media supplemented with 10% fetal bovine serum (Benchmark, Calif.) and 100 U/mL Penicillin, 100 µg/mL of Streptomycin, and 292 µg/mL L-Glutamine (Corning, N.Y.). All cultures were maintained at 37° C. in a humidified 5% $CO_2$ atmosphere and tested to ensure absence of *Mycoplasma*. Plates were treated with 0 Gy (no radiation) or with 1-10 Gy of γ-radiation delivered at 0.91 Gy/min with a $^{137}Cs$ source using a GammaCell 40 Exactor (Best Theratronics; Ontario, Canada).

Clonogenic Survival.

Cells were plated at appropriate dilutions, irradiated, and incubated for 10-14 days for colony formation. For chemical radiosensitization measurements, drug was added 24 hours prior to irradiation. Colonies were fixed in a solution of acetic acid and methanol 1:3 (v/v) and stained with 0.5% (w/v) crystal violet as previously described (15). A colony was defined to consist of 50 cells or greater. Colonies were counted digitally using ImageJ software as described (16). Integration of survival as a function of dose, or area under the curve, was calculated using Prism, GraphPad Software (La Jolla, Calif.).

High-Throughput Proliferation Assay.

Cells were plated using a Multidrop Combi liquid handler (Thermo Fisher) in quadruplicates for each time point at four cell densities (range 25-300 cells/well) in a white 384-well plate (Corning, N.Y.). Plates were irradiated and at each time point, media was aspirated and 40 µL of CellTiter-Glo® reagent (50% solution in PBS) (Promega, WI) was added to each well. Relative luminescence units were measured using an Envision multilabel plate reader (Perkin Elmer) with a measurement time of 0.1 seconds. Luminescence signal is proportional to the amount of ATP present.

Antibody and Reagents.

Anti-NRF2 antibody (ab31163) was from Abcam (Cambridge, Mass.) (17). NVP-BKM120 and TGX-221 was from Selleck (Houston, Tex.). LY 294002 was from Cell Signaling Technology (Beverly, Mass.).

RNA Interference Analysis and Generation of LC-1/SQSF, hNQO1-ARE-Luc.

Construction of the retroviral expression vector of short hairpin RNA (shRNA) was carried out as described (18). The shRNA-targeted sequences were as follows: NRF2-1 shRNA, AGAGCAAGATTTAGATCATTT (SEQ ID NO: 1); NRF2-2 shRNA, GCTCCTACTGTGATGTGAAAT (SEQ ID NO: 2). The control vector contains nontargeting shRNA sequence. The entry vectors were recombined with pLKO-Tet-ON-puro by LR reactions (Invitrogen, Carlsbad, Calif.), in accordance with the manufacturer's instructions. After infection (multiplicity of infection >1), cells were selected and maintained in the presence of 1 µg/ml puromycin.

LC-1/SQSF, hNQO1-ARE-luc cells were produced as follows. hQR41-ARE sequence (19) and firefly luciferase-PEST sequence (Promega, WI) was cloned into plenti6/BLOCK-iT-DEST lentivirus backbone (Invitrogen, NY) at the restriction sites of NcoI and Hind III. The engineered region was sequence verified and matched 100% of the expected sequences. The plasmid was stably infected to the LC-1/SQSF cell line, selected and maintained in 5 µg/ml Blasticidin in the recommended media.

TP53 and NFE2L2 Pathway Signatures.

Gene transcription signature of pathways TP53 (or p53) and NFE2L2 (or NRF2) were defined as described (20).

Single-Sample GSEA and the Information-Based Association Metric.

The single-sample GSEA enrichment scores were obtained as described.

Light Microscopy

Images were obtained by a Zeiss Axiovert 40 CFL microscope at an objective of 5×, a Zeiss Axiocam MRm camera, and the software package used was AxioVisionLE v4.7. Threshold manipulation, expansion or contraction of signal ranges, the altering of high signals, pseudo-coloring, or nonlinear adjustment was not applied.

TP53 and NFE2L2 Pathway Signatures.

Gene transcription signature of pathways TP53 (or p53) and NFE2L2 (or NRF2) were defined as described (1). p53 pathway: "IARC" signature, canonical bound and up-regulated p53 gene targets, as catalogued in the p53 IARC database (http://www-p53.1arc.fr/TargetGenes.html); "GSK" signature, from Glaxo-Smith-Kline (GSK) cell line database, coupled with "R14" p53 database of mutations in cell lines (N=248 cell lines with TP53 status), where a t-test of P<0.01 was used to determine genes higher in wild type versus mutant cell lines; "Kannan" signature, from MSigDB ("UP" targets) (2); "Troester" signature, list of genes reported repressed by TP53 knockdown in MCF7 cells (3). Nrf2 pathway: "Malhotra" signatures (4), which combined expression profiling and Chip-seq of mouse embryonic fibroblasts (MEFs) with either constitutive nuclear accumulation (Keap1−/−) or depletion (Nrf2−/−) of Nrf2, including genes downregulated in Nrf2−/− versus wild type and Nrf2 bound, and genes upregulated in Keap1−/− versus wild type and Nrf2 bound; "GSE28230," from GEO dataset of A549 adenocarcinoma lung cancer cells with siRNA knockdown of NRF2 (used P<0.01, fold>1.5); "Osburn," from GSE11287 dataset of mouse liver with or without Keap1 knockout used (P<0.01, fold>1.5).

For a given gene signature, we extracted the expression values from the CCLE dataset. For each gene, we normalized expression values to standard deviations from the median across cell lines. We computed the average normalized expression of the signature genes within each cell line in which data was available. Across the cell lines, we normalized the gene signature scores to standard deviations from the median across CCLE, and a "summary score" for each pathway was computed as the average of the individual normalized signature scores.

TP53 mRNA expression data is from CCLE (5) and was generated on Affymetrix U133Plus2 arrays. Expression values are for TP53 201746_at probe set and normalized using the MAS 5.0 algorithm,(6) with a 2% trimmed mean of 150. Single-Sample GSEA and the Information-Based Association Metric.

The association between ssGSEA profiles for each gene set and the radiation response profile was determined using an information-based similarity metric (RNMI). This quantity is obtained by estimating the differential mutual information (7) between the radiation response profile and each of the gene sets' ssGSEA profiles and then normalizing and rescaling it so that it is defined from zero (no association) to one (perfect association). We estimate the differential mutual information:

$$I(x, y) = \int\int dx dy P(x, y) \log_2 \frac{P(x, y)}{P(x)P(y)}$$

using a kernel-based method (8) which places a Gaussian density centered at each data point and a width determined by a biased cross-validation estimate (8, 9). The mutual information is then normalized (10)

$$D(x, y) = 1 - \frac{I(x, y)}{H(x, y)} = \frac{H(x) + H(y)}{H(x, y)}$$

using the joint entropy to better account for the intrinsic differences in entropy associated with each single-sample GSEA profile. Finally the normalized mutual information is rescaled using the value of the metric for the radiation response profile against itself, $$M(x, y) = \frac{I(x, y)}{H(x, y)} = \frac{H(x) + H(y)}{H(x, y)} - 1$$

In order to provide directionality to the metric we assigned a "sign" to each profile's RNMI according to the sign of the correlation coefficient, $$N(x, y) = \text{sign}(\rho(x, y)) \frac{M(x, y)}{M(x, x)}$$

The RNMI has several advantages including increase sensitivity to non-linear relationships and better resolution at the high end of the matching range. The nominal p-values for the information-based association metric scores between the gene sets/pathways and radiation response scores were estimated using an empirical permutation test.

REFERENCES

1. Curran W J. New chemotherapeutic agents: update of major chemoradiation trials in solid tumors. Oncology (Williston Park). 2002; 63 Suppl 2:29-38.
2. Hammerman P S, Janne P A, Johnson B E. Resistance to Epidermal Growth Factor Receptor Tyrosine Kinase Inhibitors in Non-Small Cell Lung Cancer. Clin Cancer Res. 2009; 15:7502-9.
3. Paez J G, Janne P A, Lee J C, Tracy S, Greulich H, Gabriel S, et al. EGFR mutations in lung cancer: correlation with clinical response to gefitinib therapy. Science. 2004; 304:1497-500.
4. Kwak E L, Bang Y J, Camidge D R, Shaw A T, Solomon B, Maki R G, et al. Anaplastic lymphoma kinase inhibition in non-small-cell lung cancer. N Engl J. Med. 2010; 363:1693-703.
5. Amundson S A, Do K T, Vinikoor L C, Lee R A, Koch-Paiz C A, Ahn J, et al. Integrating global gene expression and radiation survival parameters across the 60 cell lines of the National Cancer Institute Anticancer Drug Screen. Cancer research. 2008; 68:415-24.
6. Eschrich S, Zhang H, Zhao H, Boulware D, Lee J H, Bloom G, et al. Systems biology modeling of the radiation sensitivity network: a biomarker discovery platform. International journal of radiation oncology, biology, physics. 2009; 75:497-505.
7. Torres-Roca J F, Eschrich S, Zhao H, Bloom G, Sung J, McCarthy S, et al. Prediction of radiation sensitivity using a gene expression classifier. Cancer research. 2005; 65:7169-76.
8. Puck T T, Marcus P I. Action of x-rays on mammalian cells. J Exp Med. 1956; 103:653-66.
9. Eriksson D, Stigbrand T. Radiation-induced cell death mechanisms. Tumour Biol. 2010; 31:363-72.
10. Bardelle C, Boros J. Development of a high-content high-throughput screening assay for the discovery of ATM signaling inhibitors. Journal of biomolecular screening. 2012; 17:912-20.
11. Tseng H M, Shum D, Bhinder B, Escobar S, Veomett N J, Tomkinson A E, et al. A high-throughput scintillation proximity-based assay for human DNA ligase I V. Assay and drug development technologies. 2012; 10:235-49.
12. Katz D, Ito E, Liu F F. On the path to seeking novel radiosensitizers. International journal of radiation oncology, biology, physics. 2009; 73:988-96.

13. Auperin A, Le Pechoux C, Rolland E, Curran W J, Furuse K, Fournel P, et al. Meta-analysis of concomitant versus sequential radiochemotherapy in locally advanced non-small-cell lung cancer. J Clin Oncol. 2010; 28:2181-90.
14. Barretina J, Caponigro G, Stransky N, Venkatesan K, Margolin A A, Kim S, et al. The Cancer Cell Line Encyclopedia enables predictive modelling of anticancer drug sensitivity. Nature. 2012; 483:603-7.
15. Franken N A, Rodermond H M, Stap J, Haveman J, van Bree C. Clonogenic assay of cells in vitro. Nat. Protoc. 2006; 1:2315-9.
16. Cai Z, Chattopadhyay N, Liu W J, Chan C, Pignol J P, Reilly R M. Optimized digital counting colonies of clonogenic assays using ImageJ software and customized macros: comparison with manual counting. International journal of radiation biology. 2011; 87:1135-46.
17. Pendyala S, Moitra J, Kalari S, Kleeberger S R, Zhao Y, Reddy S P, et al. Nrf2 regulates hyperoxia-induced Nox4 expression in human lung endothelium: identification of functional antioxidant response elements on the Nox4 promoter. Free radical biology & medicine. 2011; 50:1749-59.
18. Narisawa-Saito M, Handa K, Yugawa T, Ohno S, Fujita M, Kiyono T. HPV16 E6-mediated stabilization of ErbB2 in neoplastic transformation of human cervical keratinocytes. Oncogene. 2007; 26:2988-96.
19. Moehlenkamp J D, Johnson J A. Activation of antioxidant/electrophile-responsive elements in IMR-32 human neuroblastoma cells. Archives of biochemistry and biophysics. 1999; 363:98-106.
20. Hammerman P S, Lawrence M S, Voet D, Jing R, Cibulskis K, Sivachenko A, et al. Comprehensive genomic characterization of squamous cell lung cancers. Nature. 2012.
21. Carmichael J, Degraff W G, Gamson J, Russo D, Gazdar A F, Levitt M L, et al. Radiation sensitivity of human lung cancer cell lines. Eur J Cancer Clin Oncol. 1989; 25:527-34.
22. Duchesne G M, Eady J J, Peacock J H, Pera M F. A panel of human lung carcinoma lines: establishment, properties and common characteristics. British journal of cancer. 1987; 56:287-93.
23. Itoh K, Chiba T, Takahashi S, Ishii T, Igarashi K, Katoh Y, et al. An Nrf2/small Maf heterodimer mediates the induction of phase II detoxifying enzyme genes through antioxidant response elements. Biochem Biophys Res Commun. 1997; 236:313-22.
24. Itoh K, Wakabayashi N, Katoh Y, Ishii T, Igarashi K, Engel J D, et al. Keap1 represses nuclear activation of antioxidant responsive elements by Nrf2 through binding to the amino-terminal Neh2 domain. Genes Dev. 1999; 13:76-86.
25. Jeyapaul J, Jaiswal A K. Nrf2 and c-Jun regulation of antioxidant response element (ARE)-mediated expression and induction of gamma-glutamylcysteine synthetase heavy subunit gene. Biochemical pharmacology. 2000; 59:1433-9.
26. Sjoberg L, Eriksen T E, Revesz L. The reaction of the hydroxyl radical with glutathione in neutral and alkaline aqueous solution. Radiat Res. 1982; 89:255-63.
27. Singh A, Bodas M, Wakabayashi N, Bunz F, Biswal S. Gain of Nrf2 function in non-small-cell lung cancer cells confers radioresistance. Antioxid Redox Signal. 2010; 13:1627-37.
28. McDonald J T, Kim K, Norris A J, Vlashi E, Phillips T M, Lagadec C, et al. Ionizing radiation activates the Nrf2 antioxidant response. Cancer Res. 2010; 70:8886-95.
29. Shibata T, Ohta T, Tong K I, Kokubu A, Odogawa R, Tsuta K, et al. Cancer related mutations in NRF2 impair its recognition by Keap1-Cul3 E3 ligase and promote malignancy. Proceedings of the National Academy of Sciences of the United States of America. 2008; 105:13568-73.
30. Kong A N, Owuor E, Yu R, Hebbar V, Chen C, Hu R, et al. Induction of xenobiotic enzymes by the MAP kinase pathway and the antioxidant or electrophile response element (ARE/EpRE). Drug Metab Rev. 2001; 33:255-71.
31. Lamb J. The Connectivity Map: a new tool for biomedical research. Nat Rev Cancer. 2007; 7:54-60.
32. Lamb J, Crawford E D, Peck D, Modell J W, Blat I C, Wrobel M J, et al. The Connectivity Map: using gene-expression signatures to connect small molecules, genes, and disease. Science. 2006; 313:1929-35.
33. Hassane D C, Guzman M L, Corbett C, Li X, Abboud R, Young F, et al. Discovery of agents that eradicate leukemia stem cells using an in silico screen of public gene expression data. Blood. 2008; 111:5654-62.
34. Hassane D C, Sen S, Minhajuddin M, Rossi R M, Corbett C A, Balys M, et al. Chemical genomic screening reveals synergism between parthenolide and inhibitors of the PI-3 kinase and mTOR pathways. Blood. 2010; 116:5983-90.
35. Hieronymus H, Lamb J, Ross K N, Peng X P, Clement C, Rodina A, et al. Gene expression signature-based chemical genomic prediction identifies a novel class of HSP90 pathway modulators. Cancer Cell. 2006; 10:321-30.
36. Stegmaier K, Ross K N, Colavito S A, O'Malley S, Stockwell B R, Golub T R. Gene expression-based high-throughput screening (GE-HTS) and application to leukemia differentiation. Nat. Genet. 2004; 36:257-63.
37. Stegmaier K, Wong J S, Ross K N, Chow K T, Peck D, Wright R D, et al. Signature-based small molecule screening identifies cytosine arabinoside as an EWS/FLI modulator in Ewing sarcoma. PLoS medicine. 2007; 4:e122.
38. Wei G, Twomey D, Lamb J, Schlis K, Agarwal J, Stam R W, et al. Gene expression-based chemical genomics identifies rapamycin as a modulator of MCL1 and glucocorticoid resistance. Cancer Cell. 2006; 10:331-42.
39. Gupta A K, Bakanauskas V J, Cerniglia G J, Cheng Y, Bernhard E J, Muschel R J, et al. The Ras radiation resistance pathway. Cancer Res. 2001; 61:4278-82.
40. McKenna W G, Muschel R J, Gupta A K, Hahn S M, Bernhard E J. The RAS signal transduction pathway and its role in radiation sensitivity. Oncogene. 2003; 22:5866-75.
41. Mitsuishi Y, Taguchi K, Kawatani Y, Shibata T, Nukiwa T, Aburatani H, et al. Nrf2 redirects glucose and glutamine into anabolic pathways in metabolic reprogramming. Cancer Cell. 2012; 22:66-79.
42. Barbie D A, Tamayo P, Boehm J S, Kim S Y, Moody S E, Dunn I F, et al. Systematic RNA interference reveals that oncogenic KRAS-driven cancers require TBK1. Nature. 2009; 462:108-12.
43. Available from: http://www.broadinstitute.org/msigdb/
44. Freed-Pastor W A, Prives C. Mutant p53: one name, many proteins. Genes Dev. 2012; 26:1268-86.

45. Brown J M, Wouters B G. Apoptosis, p53, and tumor cell sensitivity to anticancer agents. Cancer research. 1999; 59:1391-9.
46. Pomp J, Wike J L, Ouwerkerk U, Hoogstraten C, Davelaar J, Schrier P I, et al. Cell density dependent plating efficiency affects outcome and interpretation of colony forming assays. Radiother Oncol. 1996; 40:121-5.
47. Perez-Moreno P, Brambilla E, Thomas R, Soria J C. Squamous cell carcinoma of the lung: molecular subtypes and therapeutic opportunities. Clin Cancer Res. 2012; 18:2443-51.
48. Hayakawa K, Mitsuhashi N, Hasegawa M, Saito Y, Sakurai H, Ohno T, et al. The prognostic significance of immunohistochemically detected p53 protein expression in non-small cell lung cancer treated with radiation therapy. Anticancer research. 1998; 18:3685-8.
49. Langendijk H, Thunnissen E, Arends J W, de Jong J, ten Velde G, Lamers R, et al. Cell proliferation and apoptosis in stage III inoperable non-small cell lung carcinoma treated by radiotherapy. Radiother Oncol. 2000; 56:197-207.
50. Matsuzoe D, Hideshima T, Kimura A, Inada K, Watanabe K, Akita Y, et al. p53 mutations predict non-small cell lung carcinoma response to radiotherapy. Cancer Lett. 1999; 135:189-94.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of sensitizing a non small cell lung cancer cell to radiation, the method comprising contacting the cell with a PI3 kinase inhibitor and exposing the cell to radiation, thereby sensitizing the cell to radiation, wherein the cell comprises a NFE2L2 mutation.

2. A method of enhancing cell death or reducing proliferation in a non small cell lung cancer cell, the method comprising contacting the cell with a PI3 kinase inhibitor and exposing the cell to radiation, thereby enhancing cell death or reducing proliferation in said cell, wherein the cell comprises a NFE2L2 mutation.

3. A method of enhancing radiation sensitivity in a subject having a radiation-resistant non small cell lung cancer, the method comprising administering to the subject radiation and a PI3 kinase inhibitor, thereby enhancing the subject's sensitivity to radiation, wherein radiation resistance is characterized by detecting a NFE2L2 mutation associated with radiation resistance.

4. The method of claim 3, wherein the radiation-susceptibility of the non small cell lung cancer is characterized prior to, during, or following administration of radiation.

5. The method of claim 4, wherein the radiation-susceptibility is characterized by assaying for NRF2 activation or TP53 activation.

6. The method of claim 4, wherein radiation resistance is characterized by detecting a TP53 mutation in the subject, wherein a TP53 missense mutation identifies the neoplasia as radiation resistant and a TP53 disruptive mutation identifies the neoplasia as radiation sensitive.

7. The method of claim 5, wherein the radiation susceptibility is characterized by assaying a TP53 DNA binding domain (aa. 101-305) for mutations.

8. The method of claim 5, wherein the radiation susceptibility is characterized by detecting a TP53 mutation selected from the group consisting of W146*, E171*, Q167*, E298*, V143A, D259V, R249S, M237I, V272M, V143M, R248W, and R158G Intron (ins).

9. The method of claim 4, wherein the NFE2L2 mutation is D77V, P128L, or E79K.

10. The method of claim 1, wherein the PI3 kinase inhibitor is a PI3K alpha selective inhibitor.

11. The method of claim 10, wherein the PI3 kinase inhibitor is LY 294002 or NVP-BKM120.

12. The method of claim 1, wherein the PI3 kinase inhibitor is an inhibitory nucleic acid that reduces NRF2 expression.

13. The method of claim 12, wherein the inhibitory nucleic acid molecule is NRF2-1 shRNA, AGAGCAAGATTTAGATCATTT (SEQ ID NO: 1) and/or NRF2-2 shRNA, GCTCCTACTGTGATGTGAAAT (SEQ ID NO: 2).

14. The method of claim 1, wherein the PI3 kinase inhibitor reduces NRF2-mediated transcription.

15. The method of claim 1, further comprising characterizing radiation resistance of the cell by detecting a TP53 mutation in the cancer, wherein a TP53 missense mutation identifies the cancer as radiation resistant and a TP53 disruptive mutation identifies the cancer as radiation sensitive.

16. The method of claim 1, further comprising characterizing radiation resistance of the cell by assaying a TP53 DNA binding domain (aa. 101-305) for mutations.

17. The method of claim 1, further comprising characterizing radiation resistance of the cell by detecting a NFE2L2 mutation associated with radiation resistance.

18. A method of treating a subject with non-small cell lung cancer, the method comprising
  (a) characterizing the radiation-susceptibility of the non-small cell lung cancer by detecting a TP53 or NFE2L2 mutation in the subject; and
  (b) administering to the subject radiation and a PI3 kinase inhibitor, thereby enhancing the subject's sensitivity to radiation.

* * * * *

UNITED STATES PATENT AND TRADEMARK OFFICE
CERTIFICATE OF CORRECTION

PATENT NO. : 9,439,909 B2
APPLICATION NO. : 14/466668
DATED : September 13, 2016
INVENTOR(S) : Mohamed Abazeed et al.

Page 1 of 1

It is certified that error appears in the above-identified patent and that said Letters Patent is hereby corrected as shown below:

In the Specification

At Column 1, under STATEMENT OF RIGHTS TO INVENTIONS MADE UNDER FEDERALLY SPONSORED RESEARCH, please delete the paragraph at Lines 18-23 and replace it with the following paragraph:
This invention was made with government support under grant numbers CA009382, CA109038, CA138399, GM038627, and CA163677 awarded by The National Institutes of Health. The government has certain rights in the invention.

Signed and Sealed this
Nineteenth Day of November, 2019

Andrei Iancu
*Director of the United States Patent and Trademark Office*